(12) United States Patent
Medina-Bolivar et al.

(10) Patent No.: US 9,598,707 B2
(45) Date of Patent: Mar. 21, 2017

(54) METHOD TO INCREASE THE YIELD OF PRODUCTS IN PLANT MATERIAL

(71) Applicant: Arkansas State University, State University, AR (US)

(72) Inventors: Luis Fabricio Medina-Bolivar, Memphis, TN (US); Tianhong Yang, Jonesboro, AR (US)

(73) Assignee: Arkansas State University-Jonesboro, State University, AR (US)

( * ) Notice: Subject to any disclaimer, the term of this patent is extended or adjusted under 35 U.S.C. 154(b) by 127 days.

(21) Appl. No.: 13/784,877

(22) Filed: Mar. 5, 2013

(65) Prior Publication Data
US 2014/0147886 A1 May 29, 2014

Related U.S. Application Data

(60) Provisional application No. 61/729,659, filed on Nov. 26, 2012.

(51) Int. Cl.
| | | |
|---|---|---|
| C12P 33/20 | (2006.01) | |
| C12P 17/06 | (2006.01) | |
| C12P 17/12 | (2006.01) | |
| C12P 7/22 | (2006.01) | |
| C12P 19/02 | (2006.01) | |
| C12N 5/00 | (2006.01) | |
| C12N 5/04 | (2006.01) | |
| C12P 17/18 | (2006.01) | |
| C12P 19/46 | (2006.01) | |
| C12P 17/04 | (2006.01) | |

(52) U.S. Cl.
CPC ............. *C12P 7/22* (2013.01); *C12N 5/0025* (2013.01); *C12N 5/04* (2013.01); *C12P 17/04* (2013.01); *C12P 17/06* (2013.01); *C12P 17/188* (2013.01); *C12P 19/46* (2013.01)

(58) Field of Classification Search
CPC .. C12P 19/02; C12P 7/22; C12P 17/06; C12P 33/20; C12P 17/12; C12N 5/04; C12N 5/0025
See application file for complete search history.

(56) References Cited

U.S. PATENT DOCUMENTS 7,309,591 B2  12/2007  Bru Martinez et al.
7,666,677 B2 *  2/2010  Medina-Bolivar et al. .. 435/469

FOREIGN PATENT DOCUMENTS

EP       2256209      12/2010
WO   WO 2005012507    2/2005

OTHER PUBLICATIONS

Kovacs et al., HPLC Determination of Flavonoids in Hairy-Root Cultures of Scutellaria baicalensis Georgi, Chromatographia Supplement, vol. 60 (2004) pp. S81-S85.*
Farm Credit, High Cotton for Grape Growers, Landscapes, Winter 2009, Available Online at: www.findfarmcredit.com/farm-credit-bank-landscapes_2?cat_id=7&doc_id=168.*
Wasson et al., Silencing the Flavonoid Pathway in Medicago truncatula Inhibits Root Nodule Formation and Prevents Auxin Transport Regulation by Rhizobia, The Plant Cell, vol. 18, 1617-1629.*
Yamamoto et al., Flavonoid production in Scutellaria baicalensis callus culture, Pant Cell Tissue Organ Culture, 5 (1986) pp. 216-222.*
Wikipedia, Piceatannol, Accessed May 11, 2016, Online at: en.wikipedia.org/wiki/Piceatannol.*
Jancinova et al., The Natural Stilbenoid Piceatannol Decreases Activity and Accelerates Apoptosis of Human Neutrophils: Involvement of Protein Kinase C, Oxidative Medicine and Cellular Longevity, vol. 2013, Article ID 136539, pp. 1-8.*
Lee et al., The flavonoid resveratrol suppresses growth of human malignant pleural mesothelioma cells through direct inhibition of specificity protein 1, International Journal of Molecular Medicine, 30: 21-27, 2012.*
Lijavetzky, Diego, et al. "Synergistic effect of methyljasmonate and cyclodextrin on stilbene biosynthesis pathway gene expression and resveratrol production in Monastrell grapevine cell cultures." BMC Research Notes 2008, vol. 1, 132, 2008, pp. 1-8, XP002721220, ISSN: 1756-0500.
Condori J et al, "Induced biosynthesis of resveratrol and the prenylated stilbenoids arachidin-1 and arachidin-3 in hairy root cultures of peanut: Effects of culture medium and growth stage", Plant Physiology and Biochemistry, vol. 48, No. 5, May 1, 2010, pp. 310-318, XP027046560, Gauthier-Villars, Paris, FR ISSN: 0981-9428.
Yan, Qiong, et al., "Efficient production and recovery of diterpenoid tanshinones in Salvia miltiorrhiza hairy root cultures with in situ adsorption, elicitation and semi-continuous operation", Journal of Biotechnology 119 (2005) 416-424, 2005.
Condori J et al, "Induced biosynthesis of resveratrol and the prenylated stilbenoids arachidin-1 and arachidin-3 in hairy root cultures of peanut: Effects of culture medium and growth stage", Plant Physiology and Biochemistry 48 (2010) pp. 310-318.

(Continued)

*Primary Examiner* — Karen Cochrane Carlson
*Assistant Examiner* — Jennifer M. H. Tichy
(74) *Attorney, Agent, or Firm* — Schrantz Law Firm, PLLC; Stephen D. Schrantz

(57) ABSTRACT

A method to increase the production of products of interest in plant material including plant cultures, such as, for example, cell suspension cultures, root cultures, and hairy root cultures is provided. In one embodiment, the method is to contacting the plant material with a precursor or xenobiotic when producing a product of interest from a plant. In another embodiment the plant material is also contacted with a trapping agent. The process may also provide for contacting an elicitor of the product of interest with the plant material. An embodiment provides for contacting an elicitor, precursor and trapping agent with the plant material. The ability to produce novel compounds such as glucosides and glucuronides is provided.

11 Claims, 34 Drawing Sheets

(56) References Cited

OTHER PUBLICATIONS

Bru, R. et al., "Modified Cyclodextrins are Chemicallly Defined Glucan Inducers of Defense Responses in Grapevine Cell Cultures", Journal of Agriculture and Food Chemistry vol. 54, (2006) pp. 65-71.
Loftsson, T. et al., "Cyclodextrins and their pharmaceutical applications", International Journal of Pharmaceutics, vol. 329 (2007), pp. 1-11.
Rudolf, J. et al., "Elicitation of Resveratrol in Peanut Kernels by Application of Abiotic Stresses", Journal of Agricultural and Food Chemistry, vol. 53 (2005), pp. 10186-10192.
Szejtli, J., "Introduction and General Overview of Cyclodextrin Chemistry", Chem. Rev., vol. 98 (1998), pp. 1743-1753.
Tassoni, A., et al., "Jasmonates and Na-orthovanadate promote resveratrol production in Vitis vinifera cv. Barbera cell cultures", New Phytologist, vol. 166 (2005), pp. 895-905.
Abbott, J., et al., "Purification of Resveratrol, Arachidin-1 and Arachidin-3 from Hairy Root Cultures of Peanut (*Arachis hypogaea*) and Determination of Their Antioxidant Activity and Cytotoxicity", Biotechnol. Prog., 2010, vol. 26, No. 5, pp. 1344-1351.

\* cited by examiner trans-Resveratrol cis-Resveratrol

Piceid (polydatin)

Pterostilbene

Piceatannol

Resveratrol trimethylether

Chrysin
254.24

A

B

A

B

METHOD TO INCREASE THE YIELD OF PRODUCTS IN PLANT MATERIAL

REFERENCE TO RELATED APPLICATION

This application claims priority to previously filed and co-pending application U.S. Ser. No. 61/729,569, filed Nov. 26, 2012, the contents of which are incorporated herein by reference.

STATEMENT REGARDING FEDERALLY SPONSORED RESEARCH OR DEVELOPMENT

This invention was made with Government support from the National Science Foundation-EPSCoR (grant # EPS-0701890) and the US Department of Agriculture (award #2011-38821-30928). The Government has certain rights in the invention.

BACKGROUND

Plant products including specialized metabolites (also referred as plant secondary metabolites or plant natural products) have important applications as dietary supplements, cosmeceuticals, pharmaceuticals and agrochemicals. The term natural product refers to chemical compounds produced by a living organism. In an embodiment such compounds are small molecules. In many instances, due to the complexity of their chemical structures, the production of these products is not feasible via organic synthesis and therefore their availability depends on extraction from plant sources. In vitro plant cultures are recognized as sustainable bioproduction platforms for plant products. Indeed, high value pharmaceuticals such as taxol and ginsenosides are produced at industrial scale via cell suspension and root cultures, respectively. Efforts to increase the levels of plant products in plant cultures have been attempted by elicitation and metabolic engineering strategies. Elicitation approaches have only led to partial increases in yield particularly because of transcriptional and post-transcriptional regulatory mechanisms, such as feedback inhibition, that limit their accumulation in the plant. In many cases, these regulatory mechanisms are used by the plant to prevent their accumulation to toxic levels. Furthermore, metabolic engineering efforts have been restraint because many of the enzymes involved in the biosynthesis of high value products are currently unknown.

SUMMARY

A process is provided for increasing the amount of a product of interest in plants and plant parts and cells. A precursor of the product of interest is contacted with the plant or plant part, which may optionally include an elicitor of the product of interest. The process further provides in an embodiment for a trapping agent to prevent feedback inhibition. A process is further provided for producing derivatives by use of the precursor which may include an elicitor and/or trapping agent. Carbohydrates including glucose and glucuronic acid in an embodiment may be added by the plant material to produce a derivative of the precursor. In a still further embodiment the plant cells are hairy root tissue, in another embodiment are root cultures and in a still further embodiment are cell suspension cultures.

DESCRIPTION OF THE PREFERRED EMBODIMENTS

Figure 1:
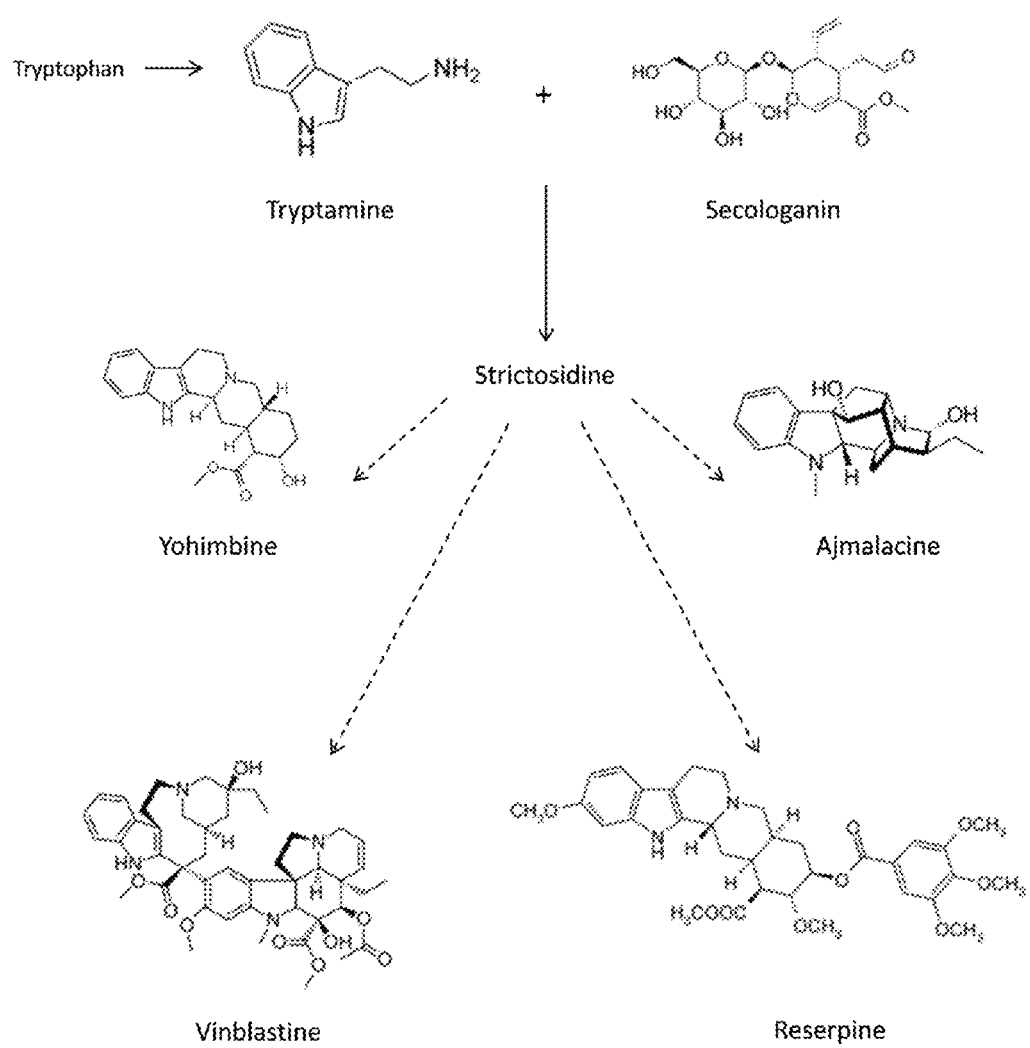
FIG. 1 is a flow chart showing an indole terpenoid alkaloid pathway.

This process addresses the problem of providing a method to produce high levels of one or more valuable products in a plant material. The solution provided by the invention is based on the addition of a putative precursor or xenobiotic to the plant culture which may also be combined with a trapping agent and also may be further combined with an elicitor.

The procedure could be applied to any plant material and is particularly useful for in vitro culture. The process is useful with plant material, including a plant, plant part, plant tissue, plant cultures, cell suspension culture or other plant material which can produce the product of interest. The term plant or plant material or plant part is used broadly herein to include any plant at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered a plant cell for purposes of this disclosure. A plant tissue or plant organ can be a seed, protoplast, callus, or any other groups of plant cells that is organized into a structural or functional unit. In an embodiment hairy root cultures or root cultures may be used as the plant material, as discussed further below. It may be used with plant material from any plant species and to any class of product. An embodiment provides the product is produced as a result of enzymatic steps in the plant. A further embodiment provides the plant optionally may be transformed with a nucleic acid molecule that encodes an enzyme that converts a substrate to the desired product.

The process may be used with any plant that produces a product of interest whether monocotyledonous or dicotyledonous or gymnosperms, including but not limited to corn (*Zea mays*), canola (*Brassica napus*, *Brassica rapa* ssp.), alfalfa (*Medicago sativa*), rice (*Oryza sativa*), rye (*Secale cereale*), sorghum (*Sorghum bicolor*, *Sorghum vulgare*), sunflower (*Helianthus annuus*), wheat (*Triticum aestivum*), soybean (*Glycine max*), tobacco (*Nicotiana tabacum*), potato (*Solanum tuberosum*), peanut (*Arachis hypogaea*), carrot (*Daucus carota*) cotton (*Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats (*Avena*), barley (*Hordeum*), radish (*Raphanus sativus*), soybean (*Glycine max*), strawberry (*Fragaria×ananassa* Duch.), vegetables, ornamentals, and conifers and medicinal and medicinally active plants including species such as hemp (*Cannabis sativa* L.), Indian mustard (*Brassica juncea* L.), *Salvia miltiorrhiza*, *Salvia austriaca*, *Withania somnifera*, *Pueraria candollei*, *Polygonum cuspidatum*, *Polygonum multiflorum*, *Scutellaria baicalensis*, *Scutellaria lateriflora*, *Scutellaria viscidula*, *Azadirachta indica*, *Panax ginseng*, *Anisodus acutangulus*, *Artemisia annua*, *Cassia obtusifolia*, *Phytolacca americana*, *Tephrosia purpurea*, licorice (*Glycyrrhiza glabra*), *Psammosilene tunicoides*, pomegranate (*Punica granatum*), *Peganum harmala*, *Sylibum marianum*, *Nicotiana benthamiana*, *Calotropis gigantean*, *Linum mucronatum*, *Linum album*, *Chenopodium murale*, *Catharanthus roseus*, black nightshade (*Solanum nigrum*), *Atropa belladonna*, *Rauvolfia verticillata*, *Panax quinquefolium*, *Aconitum coreanum*, *Coleus forskohlii*, red beet (*Beta vulgaris* L.), Egyptian henbane (*Hyoscyamus muticus*), *Arnebia euchroma* (Royle) Johnst, oriental melon (*Cucumis melo* L. cv. Geumssaragi-euncheon), muskmelon (*Cucumis melo* L.), *Latuca virosa*, *Sesamum indicum*, *Abelmoschus esculentus*, periwinkle (*Vinca minor* L.), pink periwinkle (*Catharanthus roseus* G. Don syn. *Vinca rosea* L.), *Eurycoma longifolia*, Tartary buckwheat (*Fagopyrum tataricum*), common buckwheat (*Fagopyrum esculentum* Moench), *Sapium sebiferum*, *Datura innoxia*, *Lithospermum canescens*, *Trigonella foenum*, devil's claw (*Harpagophytum procumbens*), *Angelica gigas*, *Plumbago zeylanica*, *Echinacea purpurea*, *Psammosilene tunicoides*, *Ocimum basilicum*, *Ophiorrhiza alata*, *Ophiorrhiza rugosa*, valerian (*Valeriana officinalis* L.), *Picrorhiza kurroa*, watercress (*Nasturtium officinale*), *Camptotheca acuminata*, *Pogostemon cablin*, *Taxus×media*, *Taxus* spp., annatto (*Bixa orellana*), *Veratrum californicum*.

Examples of plants that naturally produce a stilbene include *Pinus sibirica*, *Pinus sylvestris*, *Gnetum parviflorum*, *Vitis vinifera*, *Vitis rotundifolia*, *Polygonum cuspidatum*, *Arachis hypogaea*, *Eucaliptus* spp., *Artocarpus lakoocha*, *Nothofagus fusca*, *Phoenix dactilifera*, *Festuca versuta*, *Carex fedia*, *Veratrum grandiflorum*, *Cassia quinquangulata*, *Lycopersicon esculentum*, *Gossypium hirsutum* and any other plant species shown to produce resveratrol, pinosylvin or their derivatives or analogues.

As discussed further below, production of any product of interest may be enhanced using the process. Compounds in this category of products include but are not limited to phenolics, terpenoids and alkaloids. These compounds could be either produced constitutively by the plant, produced at basal levels and their biosynthesis induced by an elicitor or induced de novo upon elicitor treatment.

A product of interest or target compound produced by a plant is identified. The product of interest or target compound may be any product, including an intermediated of a desired product, produced by a plant having commercial usefulness. It may be a compound in one embodiment that is the plant produces in the presence of an eliciting substance, and in another embodiment is one produced in the absence of an eliciting substance. In an embodiment one may select a commercially useful product that is not made synthetically, or produced synthetically but at a higher cost than when produced by the plant. Examples of such products of interest without limitation are the major groups of compounds produced by plants, the phenolics, alkaloids and terpenoids. The family of compounds are related structurally and regulated by plant machinery. By way of further example without limitation, the terpenoids include diterpenes (such as taxol produced by yew plants), saponins (such as ginsenosides produced by *Panax ginseng*), sesquiterpenes (such as artemisinin produced by *Artermisia annua*). Examples, without intending to be limiting of phenolics include stilbenoids (such as arachidin-1 produced by peanut) and flavonoids (such as wogonin produced by *Scutellaria*). Examples without intending to be limiting of alkaloids include monoindole alkaloids (such as vinblastine produced by *Catharanthus roseus*), steroidal alkaloids (such as cyclopamine produced by *Veratrum californicum*), tropane alkaloids (such as hyoscyamine produced by *Hyoscyamus muticus*). In one embodiment, the processes described are particularly useful in the production of stilbenoids. A discussion of the stilbenoid compounds which can be produced by plants is provided below.

As a result of employing a precursor which may also include a trapping agent, and, where needed, an elicitor, the amount of the product of interest is increased at least ten times, at least 20 times, 30 times, 40 times, 50 times, 60 time, 70 times, 80 times, 100 times, 1000 times, 2000 times, 3000 times, 4000 times, 5000 times, 10,000 times, 250,000 times and more and amounts in-between as compared to those cultures which did not include at least a precursor, and which optionally included an elicitor and/or trapping agent as well.

Further, the inventors have discovered new compounds of commercial and medical value which can be produced using an elicitor, trapping agent and precursor. The process can produce as a product of interest, valuable derivatives of a compound. These derivatives are compounds obtained from another compound. In an embodiment, the original compound is transformed into a product of similar chemical structure. An embodiment provides production of valuable derivatives of the precursor. By way of example, a carbohydrate such as glucose or glucuronic acid is added to the precursor. By way of example without limitation, such a combination was used to add a carbohydrate to produce a glucoside or glucuronide of the precursor. Most plants when exposed to a xenobiotic compound, a foreign chemical such as a drug, or putative precursor will add glucose and store it but glucuronic acid derivatives are found in animals but rarely in plants. However, here, it was possible to add glucuronic acid to the precursor to produce glucuronides. Glucuronidation is an important biochemical process for drug metabolism in humans and to date there are no efficient means of producing these compounds. Here, with use of an elicitor, precursor and trapping agent, it is possible to produce glucuronides. Further enhancement of production of glucuronides is possible by seeding the medium with glucuronic acid.

The precursor is involved in the biosynthesis of the targeted product. When such precursor is a xenobiotic it may be any foreign compound (not produced in the plant culture) that could be biotransformed into an intermediate or product of the biosynthetic pathway of the targeted compound. Having identified the target compound, potential precursors may be identified which have a similar structure and/or are in the pathway that leads to production of the product. A similar compound, for example, may be the same chemical backbone structure, but have an additional chemical group that is modified or removed to produce the product. In an example, the compound may have a hydroxyl group attached, where the product lacks the hydroxyl group, it having been removed by a reaction in the plant. The putative precursor may then be tested to determine if it provides the enhanced production described here. When examining the pathway that leads to production of the product of interest, in an embodiment one identifies putative precursors that are closer in the pathway to the product as opposed to early in the pathway. Those compounds early in the pathway could be converted to a compound different from the desired product of interest. By way of example without limitation, if a compound is ten or twenty steps earlier in the pathway than the product of interest, it may be too early in the pathway to be a useful precursor. Those compounds, by way of example without limitation, that are one step, two steps, three steps, four steps or five steps in the pathway are useful putative precursors. Testing may then confirm its usefulness as precursors. Examples of precursors of terpenoids are acetate and squalene; examples of precursors of phenolics include phenylalanine, coumaric acid and cinnamic acid; examples of precursors of alkaloids include tryptophan and putrescine.

Figure 2:
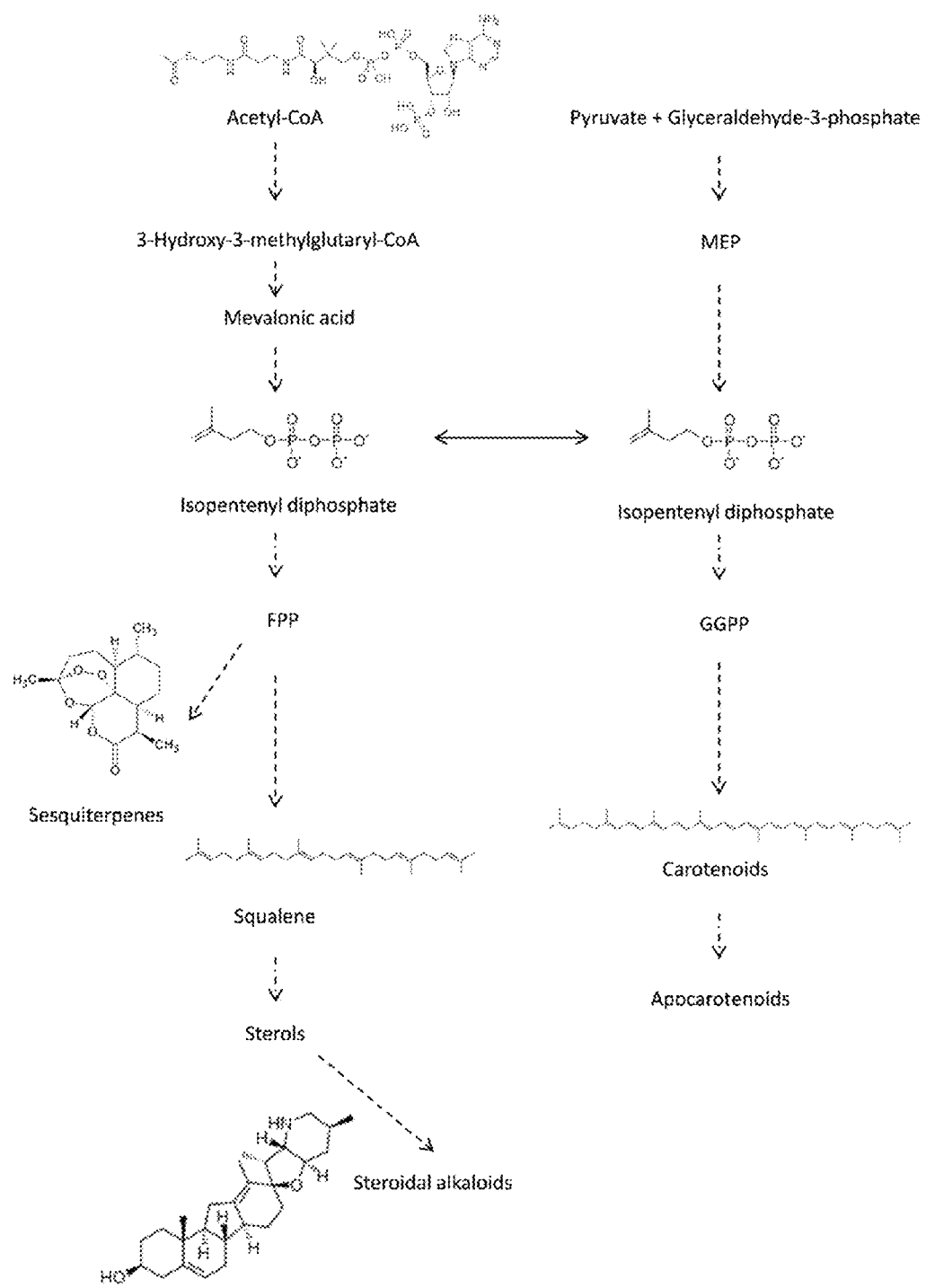
FIG. 2 is a flow chart showing an terpenoid and steroidal alkaloid pathway.
Figure 3:
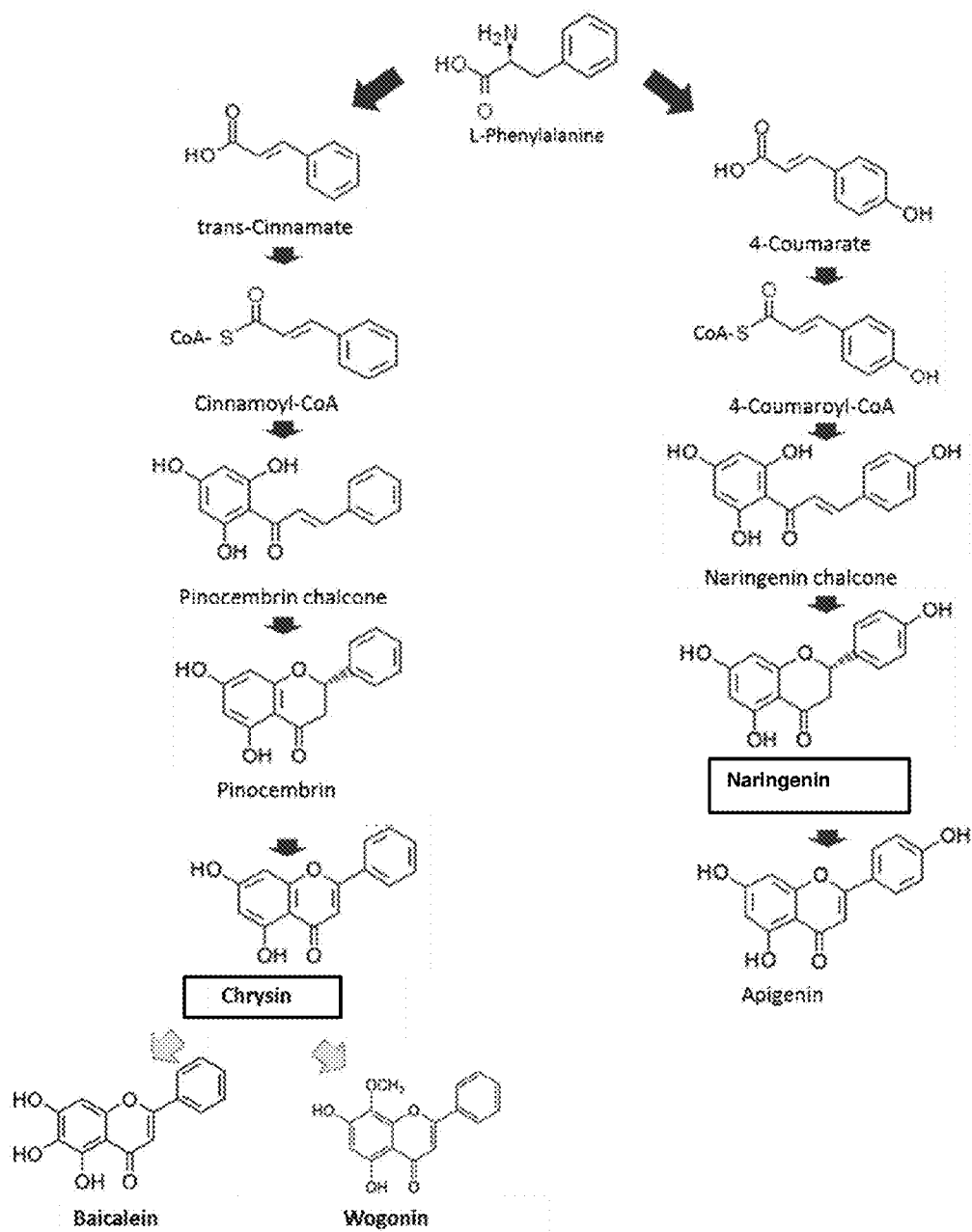
FIG. 3 is a flow chart demonstrating biosynthesis of flavonoids.

FIG. 1 shows by way of example portions of an indole terpenoid alkaloid pathway and FIG. 2 shows by way of example portions of the terpenoid and steroidal alkaloid pathways. FIG. 3 shows by way of example biosynthesis of flavonoids. Compounds indicated with a box were selected as metabolic precursors for feeding experiments in combination with cyclodextrin and methyl jasmonate.

Here it has been discovered that using at least one such precursor dramatically increases the amount of product of interest produced in the plant. Using a precursor can result in feedback inhibition of production of the product of interest. With the combination of a trapping agent disclosed here, such feedback inhibition has not limited production of the product.

In an embodiment, the ability of the precursor to substantially increase the amount of product of interest is enhanced where a trapping agent is used to aid in preventing feedback inhibition. A trapping or binding agent is one that can complex with compounds in the pathway and trap the product or intermediate. In a preferred embodiment the trapping agent is one which is not permanently bound to the product of interest.

An example of one such trapping agent, without intending to be limiting, is cyclodextrin. This family of compounds are cyclic sugars that are the result of enzyme decomposition of starch and typically have toroidal structures formed by 6 to 8 (or up to 10) glucose residues. Examples include α-, β- and γ-cyclodextrins. Cyclodextrins have been well characterized, as, for example, published by the National Office for Research and Technology providing a database at www.cyclodextrin.net and such publications as Szejli (1998) "Introduction and general overview of cyclodextrin chemistry" *Chem Rev.* 98(5):1743-1754; Loftsoon et al. (2007) "Cyclodextrins and their pharmaceutical applications" Int. J. Pharm. 329(1-1):1-11. Cyclodextrin has been used to elicit resveratrol in cell cultures (See U.S. Pat. No. 7,309,591). Without intending to be bound by a particular theory, it is believed in the present process, the cyclodextrin acts not just as an elicitor, but to prevent feedback inhibition of production of a product of interest. This soluble compound has advantage in that it is not permanently bound to the product of interest and is believed to act to prevent inhibition of the enzyme producing the downstream product, thereby allowing continuation of the biosynthetic pathway. Different types of cyclodextrin, including β-cyclodextrin, are known to make complexes with hydrophobic compounds thereby increasing their solubility. The complex of the putative precursor or xenobiotic with cyclodextrin could increase their solubility. In addition, cyclodextrins may trap toxic intermediates in the pathway or trap the desirable product thereby preventing feedback inhibition of the pathway.

Where the product or a precursor is hydrophobic, hydrophobic resin may be used. An example, without intending to be limiting, of such a resin is a polystyrene resin, such as DIAION HP-20 polystyrene resin manufactured by Supelco (Bellefonte, Pa.). This resin was described in Abbot and Medina-Bolivar et al. (2010) "Purification of resveratrol, arachidin-1 and arachidin-3 from hairy root cultures of peanut (*Arachis hypogeaea*) and determination of their antioxidant activity and cytotoxicity" American Institute of Chemical Engineers, DOI 10/1002/btpr.454, published online Jul. 7, 2010 in Wiley Online Library (wileyonlinelibrary.com). There, the resin was used to extract the stilbenoids. The resin absorbed the stilbenoids which were then extracted from the resin with ethyl acetate. Another example that could be used in tissue cultures is the hydrophobic polymeric resin X-5 which resin is described by Yan et al. (2005) in "Efficient production and recovery of diterpenoid tanshinones in *Salvia miltiorrhiza* hairy root cultures with in situ adsorption, elicitation and semi-continuous operation".

Common elicitors used in the plant cultures are jasmonic acid and its derivative methyl jasmonate. These elicitors act as signal molecules to upregulate specialized biosynthetic pathways. There are many such elicitors known to one skilled in the art and which will become available to one skilled in the art. Examples of such elicitors, without intending to be limiting, are discussed below.

Different incubation periods of the putative precursor or xenobiotic which may include the trapping agent and elicitor may be tested to obtain different levels of the targeted product.

Furthermore, cultures at different stages of development may respond differently to the treatment of the trapping agent, putative precursor or xenobiotic and elicitor. The conductivity of the culture medium could be used as an estimation of the stage of development of the plant culture. Therefore, highest production levels in response to the treatment of the trapping agent, putative precursor or xenobiotic and elicitor will depend on conducting the experiment at a particular range of conductivity values of the culture medium. An embodiment provides that for highest levels of product production, a preferred stage of growth of the plant culture is used. One may test for the preferred stage by assessing the impact of different stages of growth of the culture. Any means for measuring stage of growth of a culture may be used that is convenient. By way of example without limitation, one means of measuring the stage of hairy root culture growth is to measure conductivity. Conductivity can be measured by any convenient methods, and one example is to use a SevenEasy™ conductivity meter (Mettler Toledo). There is an inverse relationship of conductivity to growth of the culture. At the stationary phase, no change in conductivity is observed. Conductivity measures the total ionic composition change in the medium. See Condori et al. (2010) "Induced biosynthesis of resveratrol and the prenylated stilbenoids arachidin-1 and arachidin-3 in hairy root cultures of peanut: Effects of culture medium and growth stage" *Plant Physiology and Biochemistry* 48:310-318; Yang et al. (2005) "Conductivity and pH dual detection of growth profile of healthy and stressed *Listeria monocytogenes.*" *Biotechnol. Bioeng.* 92:685-694. $H^+$ and other ions may be measured. As the culture takes up nutrients, conductivity decreases. The optimal stage of culture may be an early stage, or later stage depending upon the enzymes that are developmentally expressed. In an example without intending to be limiting, Condori et al (2010), supra, measure the impact of elicitation of stilbenoids at varying growth stages of days 6, 9, 12, and 15. While varying stages produce the desired stilbenoids, trans-resveratrol, trans-arachidin-1 and trans-arachidin-3, it was found that using MSV medium produced higher levels of trans-resveratrol at all culture ages, and there was more variability in levels of trans-arachidin-1 and trans-arachidin-3 compared to resveratrol in either B5 or MSV medium. For the highest production of stilbenoids in peanut Hull3 line, use of MSV medium at day 9 resulted in the highest levels. The use of plant hairy root cultures and root cultures to produce stilbenes is discussed at length in U.S. Pat. No. 7,666,677, incorporated by reference herein in its entirety, and also at US Publication No. 20100130623, also incorporated by reference herein in its entirety.

Stilbenes, including resveratrol and pinosylvin, have garnered much interest over the past few decades due to various health benefits associated with these plant secondary metabolites. Resveratrol is a popular, natural antioxidant molecule associated with cardiovascular and anticancer health benefits. Resveratrol exists as both the trans- and cis-isomer with numerous reports suggesting trans-resveratrol to be the most bioactive form of this molecule (Roupe et al., 2006a). Trans-resveratrol can readily be converted to cis-resveratrol when exposed to UV light and is unstable when exposed to high pH conditions. In addition to the resveratrol isomers, derivatives of resveratrol that include but are not limited to glycosylated, prenylated, methylated, hydroxylated modifications as well as tetramers of resveratrol have been linked with beneficial activities. Several of these forms of resveratrol may in fact provide enhanced bioavailability and performance profiles surpassing that observed for the free resveratrol isomers (Chang et al., 2006; Roupe et al., 2006b; Wenzel and Somoza, 2005; Soleas et al., 2001). Some examples include naturally occurring monomethylether analogues of resveratrol that may be important in the inhibition of CYP1A2 and CYP2E1's potential chemopreventive activity (Mikstacka et al., 2006). Several novel and previously identified resveratrol derivatives including several vitisinols, viniferal and ε-viniferin from the roots of *Vitis thunbergii* showed significant antioxidative and antiplatelet activities (Huang et al., 2005). Recent identification of a tetrameric form of resveratrol, vaticanol B, appears to have potent anti-inflammatory properties in protecting cells against ER stress-induced cell death (Tabata et al., 2007). Arachidin-1 and -3 are prenylated derivatives of resveratrol found in peanuts and show favorable anti-inflammatory and antioxidant activities in a cell model (Chang et al., 2006). Likewise, pinosylvin and its derivatives have shown promise as anti-inflammatory and chemopreventative agents (Park et al., 2004; Lee et al., 2006). The above lists a few examples and many other derivatives are known or remained to be identified and included within the scope of the invention. While resveratrol, pinosylvin, and their respective derivatives can be recovered as an extract from a variety of plants, these products sourced from raw botanical material may not be suitable for all applications in the food/pharmaceutical sectors due to endogenous plant impurities/associated color (i.e. phenolic compounds, tannins, etc.) or production impurities (i.e. chemical residues, heavy metals, soil pathogens). In addition, these secondary metabolites are generally recovered from the raw botanical material at relatively low concentrations. Finally, stilbene yields can be highly variable from lot to lot of this raw botanical material due to the impact of environmental factors in the field.

In the '677 patent and is US publication 201030623, it was shown that plant hairy roots, produced via infection with *Agrobacterium*, offer a novel and sustainable plant tissue-based system for the bioproduction of valued secondary metabolites including the stilbenoids resveratrol, pinosylvin and their respective derivatives. These roots reflect the metabolic phenotype of the host plant, yet are unique in their genetic and biosynthetic stability, providing advantages in production sustainability when compared with plant cell culture systems. Recent progress in the scale-up of hairy root cultures, such as the use of a low cost mist bioreactor for commercial production of the anticancer camptothecin, continues to advance this system as an attractive tool for industrial processes (Wink et al., 2005; Guillon et al., 2006). Further, production of increased amounts of the trans-isomer of resveratrol as well as other valued stilbene derivatives in medium and root has been demonstrated through hairy root elicitation of this plant tissue culture platform.

Figure 4:
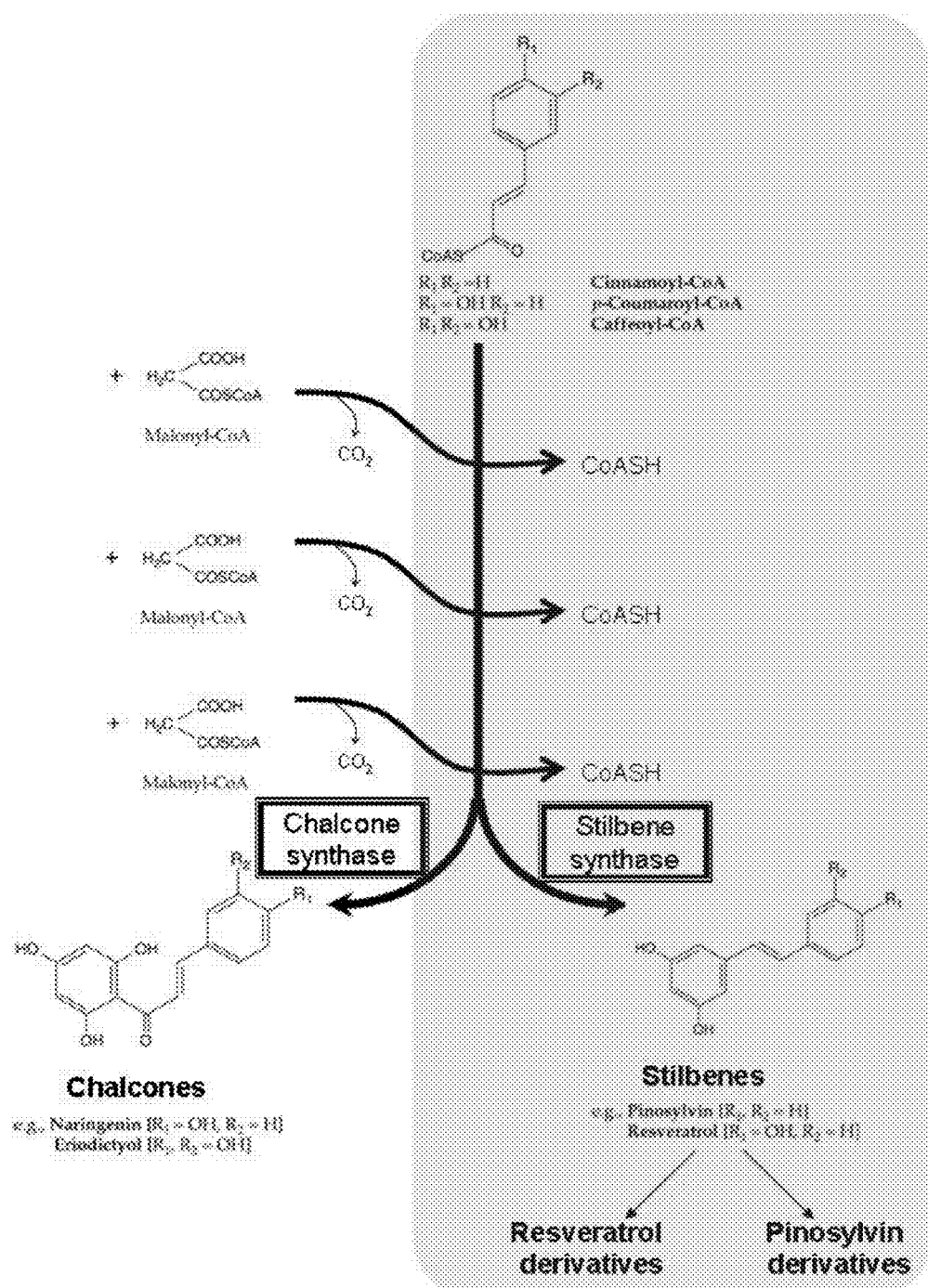
FIG. 4 is a flow chart showing a biosynthetic pathway of stilbenes, including resveratrol derivatives and pinosylvin and derivatives.
Figure 5:
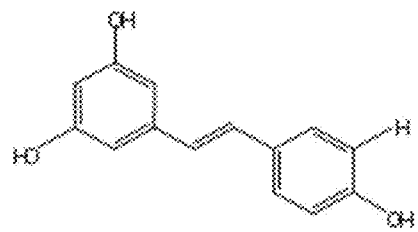
FIG. 5 is a diagram in which the chemical structures of resveratrol and select resveratrol derivatives are shown.
Figure 5:
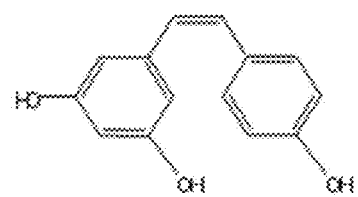
Figure 5:
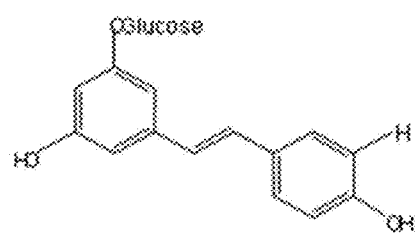
Figure 5:
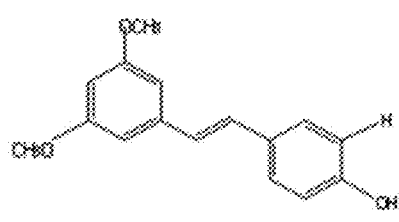
Figure 5:
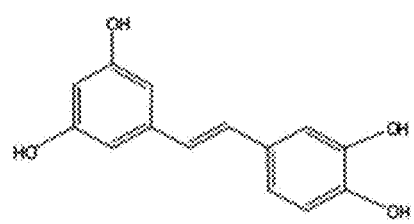
Figure 5:
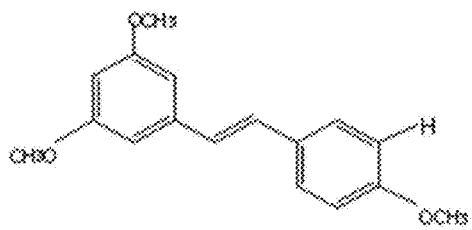

The following abbreviations are used here: B5, Gamborg's B5 medium with 2% sucrose (Gamborg et al., 1968); cv., cultivar; HPTLC, high performance thin layer chromatography; HPLC, high performance liquid chromatography; Rf, retardation factor; Rt, retention time; TLC, thin layer chromatography With establishment of hairy root cultures from a wide variety of selected plant species, the publication and patent showed that stilbenes, including resveratrol, pinosylvin and their respective derivatives can be produced without inclusion of a transgene encoding key enzymes (such as those encoding resveratrol synthase, the enzyme involved in the synthesis of resveratrol; Chun et al., 2001). These stilbenes have been reported to be produced naturally in a wide range of plant species (Aggarwal et al., 2004). What is more, hairy root cultures can also be used with plants transformed with genes encoding a stilbene synthase enzyme. Stilbenes are naturally occurring defense compounds derived from the activity of a stilbene synthase (i.e. resveratrol synthase or pinosylvin synthase). A stilbene synthase enzyme defines an important regulatory entry point to the stilbene biosynthetic pathway as shown in FIG. 4. By use of the term stilbene or stilbene composition is meant: (i) resveratrol and/or all natural resveratrol derivatives and analogues, including, for example, those shown in FIG. 5 and any other identified as derivatives of resveratrol and (ii) pinosylvin and/or all natural pinosylvin derivatives and analogues.

Since these stilbene derivatives are typically present and recoverable in only small amounts from field-grown raw botanical material, the hairy root production platform offers a viable, saleable, production alternative for naturally sourced resveratrol, resveratrol derivatives and other valued stilbenes. When referring to a resveratrol composition is meant to include resveratrol, resveratrol derivatives or combinations of same. Likewise, when referring to a pinosylvin composition is meant pinosylvin, pinosylvin derivatives, and combinations of same.

Hairy root disease was first identified as a problem in select plants caused by *Agrobacterium rhizogenes*, which can be isolated from the soil. The gram-negative bacterium transfers DNA from its root-inducing (Ri) plasmid into the genome of the infected plant cell which results in the formation of roots. Its use in the control of beneficial growth of roots was described by Strobel, U.S. Pat. No. 4,588,693. In the production of hairy root cultures, the plant is infected with the *Agrobacterium* by exposure of plant cells or plant parts to *Agrobacterium*. For example, The rol genes containing genes rolA, rolB and rolC (F. F. White et al., (1985)) are present in the T-DNA of *Agrobacterium rhizogenes* Ri plasmid and expression of these genes induce the formation of hairy roots. Any plant part, tissue or cell capable of producing hairy roots can be used. Such plant parts can include, for example and without limitation, plant stem, petiole, cotyledonary node, hypocotyl, or other plant parts or cells. A semi-solid medium or liquid nutrient solution is preferably employed which is optimized for maintenance of roots, resulting in increased growth rate of roots compared to non-infected plant cells. While many types of material and solutions and medium are known and can be used in the invention, several preferred examples include Murashige and Skoog and Gamborg B5 medium. Several media modifications optimized for meeting in vitro nutrient requirements of different host plants used in making sustainable hairy root cultures can be employed.

Further, the patent and publication show vectors for producing hairy roots in plants, which contain both the rol genes and aux genes in a single transfer DNA (T-DNA). This vector allows sustained growth of the hairy root line without the use of auxins since both rol and aux genes are inserted in the same plant cell DNA. Screening for several lines of hairy roots results in identification of a line that can sustain growth in liquid after several subculturing events on semi-solid medium. A vector with both rol and aux genes reduces the time in obtaining stable high growth/stilbene-secreting hairy roots. Such vectors can be used in *A. tumefaciens*, such as strains EHA105 and LBA4404 or *A. rhizogenes* strains such as R1000 and ATCC 15834.

The hairy roots are then exposed to an elicitory substance to produce the stilbenoid compounds including resveratrol, pinosylvin, and associated derivatives of these molecules. A vast number of elicitors are known to one skilled in the art, as set forth, for example, at Raskin, US publication no. 20020132021. Among elicitors known to be effective in eliciting resveratrol are the cyclodextrins, including randomly methylated β-cyclodextrin, cellulase, laminarin, chitosan, sodium acetate, copper sulfate, ultraviolet light, jasmonates, sodium orthovanadate (Rudolf and Resurreccion, 2005; Tassoni et al., 2005; Bru et al., 2006). While certain elicitors may produce optimum results, the person skilled in the art will appreciate that a number of different elicitors are available for use in the invention.

Resveratrol, pinosylvin, and derivatives may be obtained from the roots, medium or solution and extracted by known procedures, and the invention is not limited by any particular extraction procedure. For example, column chromatography, crystallization, distillation, liquid or solid phase extraction are among many techniques known in the art. An example of one such process is use of a solvent which can create two phases capable of separation, such as ethyl acetate. This provides advantages over use of solvents such as methanol, where drying is required because methanol and water are miscible and two phases are not produced. However, since the media used may be rich in sugars these can bind some of the stilbenoids, resveratrol and pinosylvin, causing a drastic decrease in recovery.

Further, the inventors have discovered that root cultures can be used to produce stilbenoids, and are effective in producing increased amounts of derivatives. The term root cultures herein is referring to a root culture other than hairy root cultures, and are those which do not require infection with *Agrobacterium* nor require introduction of an Agrobacteria gene(s) as with production of hairy root cultures. Root cultures which can be used to produce stilbenes or other compounds are a proliferating root culture system derived from root tips of apical or lateral origin grown under sterile (in vitro) or non-sterile conditions that do not require infection with *Agrobacterium*. The root tips or biomass are derived from roots of seedlings, plantlets, hydroponically-grown plants or any plant explant or callus induced to produce roots. Production of stilbene or other target composition can be increased in an embodiment by increasing production of the root cultures, exposing the culture to chemical or physical stimulus or by genetic modification of the roots. The stilbene composition may be in a further embodiment isolated from roots or root culture media and in an embodiment may be purified by known processes such as chromatography and chemical solvent extraction, for example. In one embodiment, in order to increase root biomass, in vitro isolated root cultures (adventitious root cultures) are supplemented with exogenous auxin hormone(s) [e.g. indole acetic acid (IAA), naphthalene acetic acid (NAA), indole butyric acid (IBA), 2,4-dichlorophenoxyacetic acid (2,4-D)]. Alternatively hormones are provided directly from the system in the case of root cultures derived from hydroponically-grown plants. In such root cultures the root biomass may likewise be produced in batch cultures and/or bioreactors as described herein.

Thus, as discussed above, stilbene is produced, stilbene having a common backbone structure consisting of a hydrocarbon with a trans or cis ethane double bond substituted with a phenyl group on both the carbon atoms of the double bond. Such stilbene derivatives include precursors and analogs and, for example, but without limitation, include glycosylated, prenylated, methylated and hydroxylated modifications as well as oligomers and polymers of same. Further specific examples, without meant to be limiting, include trans- and cis-resveratrol, piceid, arachidin including arachidin-1 and 3, vitisinols, viniferal and E-viniferin, vaticanol B, pinosylvin derivatives, among others. Increased production of valuable derivatives provides for an enhanced activity of such stilbene compositions. Compositions having increased stilbene derivatives compared to resveratrol have particular advantages and medical and health enhancing benefits. Benefits are particularly useful where the amount of derivative produced in the composition compared to resveratrol is at least ten times as much, at least 20 times as much, at least 30 times as much, at least 40 times as much, at least 50 times as much, at least 100 times as much, at least 1000 times at much and any amount in between.

Assay and analysis of resveratrol may be conducted through any variety of methods, and can include, for example, taking advantage of natural fluorescence of the compound when exposed to ultraviolet light. Thin layer chromatography, high performance thin layer chromatography (Babu et al., 2005), high performance liquid chromatography, and gas chromatography-mass spectrometry are among the examples of assays that may be used to assay the resveratrol produced.

Reference to plants includes whole plants as well as plant cells and plant parts such as tissues, or protoplasts from the plant or organism, cell cultures, tissue cultures, calli, embryos, and seeds. Plants that are particularly useful are those naturally producing resveratrol, which include *Pinus sibirica, Pinus sylvestris, Gnetum parviflorum, Vitis vinifera, Vitis rotundifolia, Polygonum cuspidatum, Arachis hypogaea, Eucaliptus* sp., *Artocarpus lakoocha, Nothofagus fusca, Phoenix dactilifera, Festuca versuta, Carex fedia, Veratrum grandiflorum, Cassia quinquangulata, Lycopersicon esculentum, Gossypium hirsutum* and any other plant species shown to produce resveratrol. In a preferred embodiment of the invention the plant is *Arachis hypogaea*. In another preferred embodiment the plant is *Vitis rotundifolia*. In another preferred embodiment the plant is *Polygonum cuspidatum*. In another preferred embodiment stilbenes are produced from non-transgenic *Nicotiana*, such as *Nicotiana benthamiana*.

As described in the patent and publication, one may also employ in the process a plant which does not naturally produce stilbenes including resveratrol and pinosylvin, but which has been genetically engineered so that it produces stilbenes. As discussed herein, any plant that can be genetically engineered could be transformed with a nucleotide sequence expressing a stilbene synthase (i.e. resveratrol synthase or pinosylvin synthase). In an additional embodiment, a plant may be genetically engineered to co-express a stilbene synthase (i.e. resveratrol synthase or pinosylvin synthase) with one or more genes involved in the production of a resveratrol or pinosylvin derivative. For example, Hall and De Luca (2001) cloned a glucosyl transferase from Concord grape (*Vitis labrusca*) that can use resveratrol as substrate. In one example, co-expression of resveratrol synthase and this resveratrol glucosyl transferatese can lead to the production of resveratrol glucosides. Hall and De Luca also show that resveratrol glucosyl transferase can use different phenolic compounds as substrates. Because many of the enzymes catalyzing the downstream modifications of resveratrol or pinosylvin may also accept different phenolic compounds as substrates, one may predict that other enzymes that also use as substrates other phenolic compounds may also accept resveratrol or pinosylvin and produce resveratrol or pinosylvin derivatives. These enzymes are not limited to glucosyl transferases, prenyltransferases, methyltransferases and hydroxylases. Specific examples of these enzymes are flavonoid-O-methyltransferases, caffeoyl-CoA methyltransferase, cinnamoyl-CoA methyltransferase, geranyltransferase and any other enzyme that could accept a stilbenes compound as substrate. Using general plant transformation methods, genes encoding these enzymes could be co-expressed with a stilbene synthase or express in a transgenic plant already expressing a stilbene synthase. In addition, plants naturally producing stilbenes can be engineered with an enzyme to produce a specific class of derivative and hairy roots can be produced from these engineered plants.

Plants transformed with a gene encoding a stilbene synthase, for example resveratrol synthase or pinosylvin synthase, include any plant capable of being so transformed, including, without limitation, plants that may be used for food and feed, such as corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), potato (*Solanum tuberosum*); and peas (*Lathyrus* spp.). Alternatively, the transgenic plant may be a species that is not conventionally eaten, such as tobacco (*Nicotiana tabacum*), tea (*Camellia sinensis*), flax (*Linum*), sisal (*Agave sisalana*), firs, and cedars. Production of transgenic plants with a nucleotide sequence encoding resveratrol synthase is known, such as that discussed at Paiva et al., U.S. Pat. No. 6,974,895 and Chia et al. US publication no. 20040111760. The resulting transgenic plant or plant cell can then be induced to produce hairy roots using the process of the invention, and resveratrol or other stilbenoids could be recovered. Further, one appreciates that it falls within the scope of the invention to introduce into plant cells other desirable nucleotide sequences and then produce hairy roots from the plant cells, whether the plant naturally produces resveratrol, pinosylvin or related derivatives or is genetically engineered to produce these secondary metabolites.

In general, the methods available for construction of recombinant genes, optionally comprising various modifications for improved expression, can differ in detail. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., 1989. *Molecular Cloning: A*

*Laboratory Manual*, 2<sup>nd</sup> Edition. Cold Spring Harbor Laboratory Press, Plainview, N.Y.).

A vector is typically prepared comprising the gene encoding a molecule, such as stilbene synthase, which produces stilbenoids or the precursor or target product or intermediary product, a promoter that will drive expression of the gene in the plant and a terminator region. In this regard, any plant-compatible promoter elements can be employed in the construct, influenced by the end result desired. Those can be plant gene promoters, such as, for example, the promoter for the small subunit of ribulose-1,5-bis-phosphate carboxylase, or promoters from the tumor-inducing plasmids from *Agrobacterium tumefaciens*, such as the nopaline synthase and octopine synthase promoters, or viral promoters such as the cauliflower mosaic virus (CaMV) 19S and 35S promoters or the figwort mosaic virus 35S promoter. See Kay et al., (1987) *Science* 236:1299 and European patent application No. 0 342 926; the barley lipid transfer protein promoter, LTP2 (Kalla et al., *Plant J.* (1994) 6(6): 849-60); the ubiquitin promoter (see for example U.S. Pat. No. 5,510,474); the END2 promoter (Linnestad et al. U.S. Pat. No. 6,903,205); and the polygalacturonase PG47 promoter (See Allen and Lonsdale, *Plant J.* (1993) 3:261-271; WO 94/01572; U.S. Pat. No. 5,412,085) and rice actin promoter (McElroy et al. (1990) *Plant Cell* 2:163-171). See international application WO 91/19806 for a review of various plant promoters also suitably employed in plant gene expression.

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods.

Any inducible promoter can be used in connection with a gene expressing a molecule. See Ward et al. *Plant Mol. Biol.* 22: 361-366 (1993). Exemplary inducible promoters include ecdysone receptor promoters, U.S. Pat. No. 6,504,082; promoters from the ACE1 system which responds to copper (Mett et al. *PNAS* 90: 4567-4571 (1993)); In2-1 and In2-2 gene from maize which respond to benzenesulfonamide herbicide safeners (U.S. Pat. No. 5,364,780; Hershey et al., *Mol. Gen. Genetics* 227: 229-237 (1991) and Gatz et al., *Mol. Gen. Genetics* 243: 32-38 (1994)); the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156).

Tissue-preferred promoters can be utilized to target enhanced transcription and/or expression within a particular plant tissue. Promoters may express in the tissue of interest, along with expression in other plant tissue, may express strongly in the tissue of interest and to a much lesser degree than other tissue, or may express highly preferably in the tissue of interest. A tissue specific promoter with preferential expression in hairy roots is preferred. Such a promoter is for example the Super P promoter which harbors elements from the mannopine synthase and octopine synthase genes. This promoter has been shown to have strong expression in hairy root and low in leaves (Nopo-Olazabal et al., 2005). There are a wide variety of other tissue-preferred promoters and, by way of example, include those described in Yamamoto et al. (1997) *Plant J.* 12(2): 255-265; Kawamata et al. (1997) *Plant Cell Physiol.* 38(7): 792-803; Hansen et al. (1997) *Mol. Gen Genet.* 254(3):337-343; Russell et al. (1997) *Transgenic Res.* 6(2): 157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20: 181-196; Orozco et al. (1993) *Plant Mol Biol.* 23(6): 1129-1138; Matsuoka et al. (1993) *Proc Natl. Acad. Sci. USA* 90(20): 9586-9590; and Guevara-Garcia et al. (1993) *Plant J.* 4(3): 495-505.

Other components of the vector may be included, also depending upon intended use of the gene. Examples include selectable markers, targeting or regulatory sequences, stabilizing or leader sequences, introns etc. General descriptions and examples of plant expression vectors and reporter genes can be found in Gruber, et al., "Vectors for Plant Transformation" in *Method in Plant Molecular Biology and Biotechnology*, Glick et al eds; CRC Press pp. 89-119 (1993). The selection of an appropriate expression vector will depend upon the host and the method of introducing the expression vector into the host. The expression cassette may also include at the 3' terminus of the heterologous nucleotide sequence, a transcriptional and translational termination region functional in plants. Convenient termination regions are available from the Ti-plasmid of *A. tumefaciens*, such as the octopine synthase and nopaline synthase (nos) termination regions (Depicker et al., *Mol. and Appl. Genet.* 1:561-573 (1982)). See also, Guerineau et al. *Mol. Gen. Genet.* 262:141-144 (1991); Proudfoot, *Cell* 64:671-674 (1991); Sanfacon et al. *Genes Dev.* 5:141-149 (1991); Mogen et al. *Plant Cell* 2:1261-1272 (1990); Munroe et al. *Gene* 91:151-158 (1990); Ballas et al. *Nucleic Acids Res.* 17:7891-7903 (1989); Joshi et al. *Nucleic Acid Res.* 15:9627-9639 (1987).

Selectable reporter genes for selection of transformed cells or tissues can be included in the transformation vectors. These can include genes that confer antibiotic resistance or resistance to herbicides. Examples of suitable selectable marker genes include, but are not limited to, genes encoding resistance to chloramphenicol, Herrera Estrella et al. *EMBO J.* 2:987-992 (1983); methotrexate, Herrera Estrella et al. *Nature* 303:209-213 (1983); Meijer et al. *Plant Mol. Biol.* 16:807-820 (1991); hygromycin, Waldron et al. *Plant Mol. Biol.* 5:103-108 (1985), Zhijian et al. *Plant Science* 108: 219-227 (1995); streptomycin, Jones et al. *Mol. Gen. Genet.* 210:86-91 (1987); spectinomycin, Bretagne-Sagnard et al. *Transgenic Res.* 5:131-137 (1996); bleomycin, Hille et al. *Plant Mol. Biol.* 7:171-176 (1990); sulfonamide, Guerineau et al. *Plant Mol. Biol.* 15:127-136 (1990); bromoxynil, Stalker et al. *Science* 242:419-423 (1988); glyphosate, Shaw et al. *Science* 233:478-481 (1986); and phosphinothricin, DeBlock et al. *EMBO J.* 6:2513-2518 (1987). The latter is the phosphinothricin acetyl transferase ("PAT") or maize optimized PAT or bar gene which confers resistance to bialaphos (Gordon-Kamm. 1990. *The Plant Cell* 2: 603; Uchimiya et al. 1993. Bio/Technology 11: 835; and Anzai et al, 1989. *Mol. Gen. Gen.* 219: 492).

Scorable or screenable markers may also be employed, where presence of the sequence produces a measurable product. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. *The EMBO Journal* vol. 6 No. 13 pp. 3901-3907); and alkaline phosphatase. Other screenable markers include the anthocyanin/flavonoid genes in general (See discussion at Taylor and Briggs, *The Plant Cell* (1990) 2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., *Plant Cell* (1996) 8: 1171-1179; Scheffler et al. *Mol. Gen. Genet.* (1994) 242:40-48) and maize C2 (Wienand et al., *Mol. Gen. Genet.* (1986) 203:202-207); the B gene (Chandler et al., *Plant Cell* (1989) 1:1175-1183), the p1 gene (Grotewold et al, *Proc. Natl. Acad. Sci USA* (1991) 88:4587-4591; Grotewold et al., *Cell* (1994) 76:543-553; Sidorenko et al., *Plant Mol. Biol.* (1999)39:11-19); the bronze locus genes (Ralston et al., *Genetics* (1988) 119:185-197; Nash et al., *Plant Cell* (1990) 2(11): 1039-1049), among others. Yet further examples of suitable markers include the cyan fluorescent protein (CYP) gene (Bolte et al. (2004) *J. Cell Science* 117: 943-54 and Kato et al. (2002) *Plant Physiol* 129: 913-42), the yellow fluorescent protein gene (Phi-YFP™ from Evrogen; see Bolte et al. (2004) *J. Cell Science* 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) *EMBO J.* 8:343); a green fluorescent protein (GFP) gene (Sheen et al., *Plant J.* (1995) 8(5):777-84); and DsRed genes where plant cells transformed with the marker gene are red in color, and thus visually selectable (Dietrich et al. (2002) *Biotechniques* 2(2):286-293). Additional examples include a β-lactamase gene (Sutcliffe, *Proc. Nat'l. Acad. Sci. U.S.A.* (1978) 75:3737), which encodes an enzyme for which various chromogenic substrates are known (e.g., PADAC, a chromogenic cephalosporin); a xylE gene (Zukowsky et al., *Proc. Nat'l. Acad. Sci. U.S.A.* (1983) 80:1101), which encodes a catechol dioxygenase that can convert chromogenic catechols; an α-amylase gene (Ikuta et al., *Biotech.* (1990) 8:241); and a tyrosinase gene (Katz et al., *J. Gen. Microbiol.* (1983) 129:2703), which encodes an enzyme capable of oxidizing tyrosine to DOPA and dopaquinone, which in turn condenses to form the easily detectable compound melanin. Clearly, many such markers are available to one skilled in the art.

The expression cassettes can additionally contain 5' leader sequences. Such leader sequences can act to enhance translation. Translation leaders are known in the art and include by way of example, picornavirus leaders, EMCV leader (Encephalomyocarditis 5' noncoding region), Elroy-Stein et al. *Proc. Nat. Acad. Sci. USA* 86:6126-6130 (1989); potyvirus leaders, for example, TEV leader (Tobacco Etch Virus), Allison et al.; MDMV leader (Maize Dwarf Mosaic Virus), *Virology* 154:9-20 (1986); human immunoglobulin heavy-chain binding protein (BiP), Macejak et al. *Nature* 353:90-94 (1991); untranslated leader from the coat protein mRNA of alfalfa mosaic virus (AMV RNA 4), Jobling et al. *Nature* 325:622-625 (1987); Tobacco mosaic virus leader (TMV), Gallie et al. (1989) *Molecular Biology of RNA*, pages 237-256; and maize chlorotic mottle virus leader (MCMV) Lommel et al. *Virology* 81:382-385 (1991). See also Della-Cioppa et al. *Plant Physiology* 84:965-968 (1987).

The cassette can also contain sequences that enhance translation and/or mRNA stability such as introns. Other modifications can improve expression, include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, *Zea mays* Brittle-1 chloroplast transit peptide (Nelson et al. *Plant Physiol* 117(4):1235-1252 (1998); Sullivan et al. *Plant Cell* 3(12):1337-48; Sullivan et al., *Planta* (1995) 196(3):477-84; Sullivan et al., *J. Biol. Chem.* (1992) 267 (26):18999-9004) and the like. One skilled in the art will readily appreciate the many options available in expressing a product to a particular organelle. For example, the barley alpha amylase sequence is often used to direct expression to the endoplasmic reticulum (Rogers, *J. Biol. Chem.* 260: 3731-3738 (1985)). Use of transit peptides is well known (e.g., see U.S. Pat. Nos. 5,717,084; 5,728,925).

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions, such as transitions and transversions, can be involved.

In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra).

The method of transformation/transfection is not critical notion; various methods of transformation or transfection are currently available. As newer methods are available to transform crops or other host cells they may be directly applied. Accordingly, a wide variety of methods have been developed to insert a DNA sequence into the genome of a host cell to obtain the transcription or transcript and translation of the heterologous sequence. Thus, any method which provides for efficient transformation/transfection may be employed.

Methods for introducing expression vectors into plant tissue available to one skilled in the art are varied and will depend on the plant selected. Procedures for transforming a wide variety of plant species are well known and described throughout the literature. See, for example, Miki et al, "Procedures for Introducing Foreign DNA into Plants" in *Methods in Plant Molecular Biotechnology*, supra; Klein et al, *Bio/Technology* 10:268 (1992); and Weising et al., *Ann. Rev. Genet.* 22: 421-477 (1988). For example, the DNA construct may be introduced into the genomic DNA of the plant cell using techniques such as microprojectile-mediated delivery, Klein et al., *Nature* 327: 70-73 (1987); electroporation, Fromm et al., *Proc. Natl. Acad. Sci.* 82: 5824 (1985); polyethylene glycol (PEG) precipitation, Paszkowski et al., *EMBO J.* 3: 2717-2722 (1984); direct gene transfer WO 85/01856 and EP No. 0 275 069; in vitro protoplast transformation, U.S. Pat. No. 4,684,611; and microinjection of plant cell protoplasts or embryogenic callus, Crossway, *Mol. Gen. Genetics* 202:179-185 (1985). Co-cultivation of plant tissue with *Agrobacterium tumefaciens* is another option, where the DNA constructs are placed into a binary vector system. See e.g., U.S. Pat. No. 5,591,616; Ishida et al., "High Efficiency Transformation of Maize (*Zea mays* L.) mediated by *Agrobacterium tumefaciens*" *Nature Biotechnology* 14:745-750 (1996). The virulence functions of the *Agrobacterium tumefaciens* host will direct the insertion of the construct into the plant cell DNA when the cell is infected by the bacteria. See, for example Horsch et al., *Science* 233: 496-498 (1984), and Fraley et al., *Proc. Natl. Acad. Sci.* 80: 4803 (1983).

Standard methods for transformation of canola are described at Moloney et al. "High Efficiency Transformation of *Brassica napus* using *Agrobacterium* Vectors" *Plant Cell Reports* 8:238-242 (1989). Corn transformation is described by Fromm et al, *Bio/Technology* 8:833 (1990) and Gordon-Kamm et al, supra. *Agrobacterium* is primarily used in dicots, but monocots can be transformed by *Agrobacterium*. See supra and U.S. Pat. No. 5,550,318. Rice transformation is described by Hiei et al., "Efficient Transformation of Rice (*Oryza sativs* L.) Mediated by *Agrobacterium* and Sequence Analysis of the Boundaries of the T-DNA" The Plant Journal 6(2): 271-282 (1994, Christou et al, *Trends in Biotechnology* 10:239 (1992) and Lee et al, *Proc. Nat'l Acad. Sci. USA* 88:6389 (1991). Wheat can be transformed by techniques similar to those used for transforming corn or rice. *Sorghum* transformation is described at Casas et al, supra and *sorghum* by Wan et al, *Plant Physicol.* 104:37 (1994). Soybean transformation is described in a number of publications, including U.S. Pat. No. 5,015,580.

When referring to "introduction" of the nucleotide sequence into a plant, it is meant that this can occur by direct transformation methods, such as *Agrobacterium* transformation of plant tissue, microprojectile bombardment, electroporation, or any one of many methods known to one skilled in the art; or, it can occur by crossing a plant having the heterologous nucleotide sequence with another plant so that progeny have the nucleotide sequence incorporated into their genomes. Such breeding techniques are well known to one skilled in the art. For a discussion of plant breeding techniques, see Poehlman (1995) *Breeding Field Crops*. AVI Publication Co., Westport Conn., 4$^{th}$ Edit. Backcrossing methods may be used to introduce a gene into the plants. This technique has been used for decades to introduce traits into a plant. An example of a description of this and other plant breeding methodologies that are well known can be found in references such as Poelman, supra, and *Plant Breeding Methodology*, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

Scale up of the production of molecules from hairy root cultures may be achieved by any of the known systems for plant propagation, and the invention is not limited by the means of increasing production of resveratrol and other stilbenes. For example, an airlift mesh-draught is one example (Caspeta et al. 2005); another uses a mesh support system (Ramakrishnan et al., 2004). A bioreactor system is further described below. One skilled in the art appreciates that there are many variations on the components and processes with which the nucleotide sequence of the invention may be used. See in U.S. Pat. No. '677 and US publication 201030623 the figures and examples for illustrations of methods for producing stilbenes in plants.

The following examples are presented by way of illustration and are not intended to be limiting. All references cited herein are incorporated herein by reference.

Example 1

Biosynthesis Enhancement of Arachidin-1 in Hairy Root Cultures of Peanut

Stilbenoids are polyphenolic compounds with important applications in human health. These natural products exhibit antioxidant, anti-inflammatory and anticancer properties. Resveratrol, a stilbenoid produced by certain plant species such as grape and peanut, has been the most studied among this group of polyphenolic compounds. Previously we demonstrated the application of hairy root cultures as bioproduction system for stilbenoids including resveratrol and its analogs and derivatives. Indeed, we showed that hairy root cultures of peanut can produce resveratrol and several prenylated stilbenoids, including arachidin-1 and arachidin-3, upon treatment with sodium acetate. We further described the purification of arachidin-1 and arachidin-3 from the medium of sodium acetate-treated hairy root cultures using centrifugal partition chromatography chromatography (CPC). In a recent study we showed that arachidin-1 and arachidin-3 have affinity to cannabinoid receptors. See US Published patent application No. 20120165281 incorporated herein by reference in its entirety. Compounds that modulate cannabinoid receptor have applications in neuroprotection, control of obesity and drug addiction. Furthermore, we also demonstrated that arachidin-1 has higher antioxidant activities than resveratrol in vitro. Our recent study with arachidin-1 and arachidin-3 demonstrated that these prenylated stilbenoids have favorable metabolic profiles in vitro when compared to resveratrol. See US Published patent application No. 20120165281. Because of their higher lipophilicity and favorable metabolic profiles, the arachidins may be more bioavailable than resveratrol. Whereas resveratrol is commercially available as a synthetic and natural product, arachidin-1 and arachidin-3 are not available through any commercial sources. Studies with these stilbenoids have only been conducted extracting these polyphenols from peanut seeds challenged with fungus or peanut hairy roots treated with elicitors. Due to the importance of the arachidins, in particular arachidin-1, we designed strategies to increase the levels of this compound in peanut hairy root cultures.

Hairy roots of peanut cv. Hull line 3 were cultured for 9 days in a modified Murashige & Skoog medium at 28° C., under shaking (90 rpm) and continuous darkness. At day 9, the spent medium was removed and the conductivity of the medium was measured. The spent medium was replaced with fresh medium containing 7.5 mM of β-cyclodextrin (trapping agent) and 100 µM methyl jasmonate (MeJA, inducer) with or without 1 mM piceatannol (putative biosynthetic precursor or xenobiotic). Control cultures included ethanol (solvent of MeJA) only. Cultures were incubated for additional 24 hours as described above and then the medium was collected. The stilbenoids were extracted from the culture medium with ethyl acetate and this organic fraction was dried to completeness under nitrogen stream. The extract was resuspended in methanol and analyzed by reversed phase HPLC. Detection was done with a photodiode array detector. Arachidin-1 was confirmed by comparison to the retention time and UV spectrum of an authentic arachidin-1 standard. In addition, previous analyses by mass spectrometry confirmed the presence of arachidin-1 in induced hairy root cultures of peanut. Quantification of arachidin-1 was done by HPLC using a calibration curve of authentic arachidin-1 standards.

Figure 6:
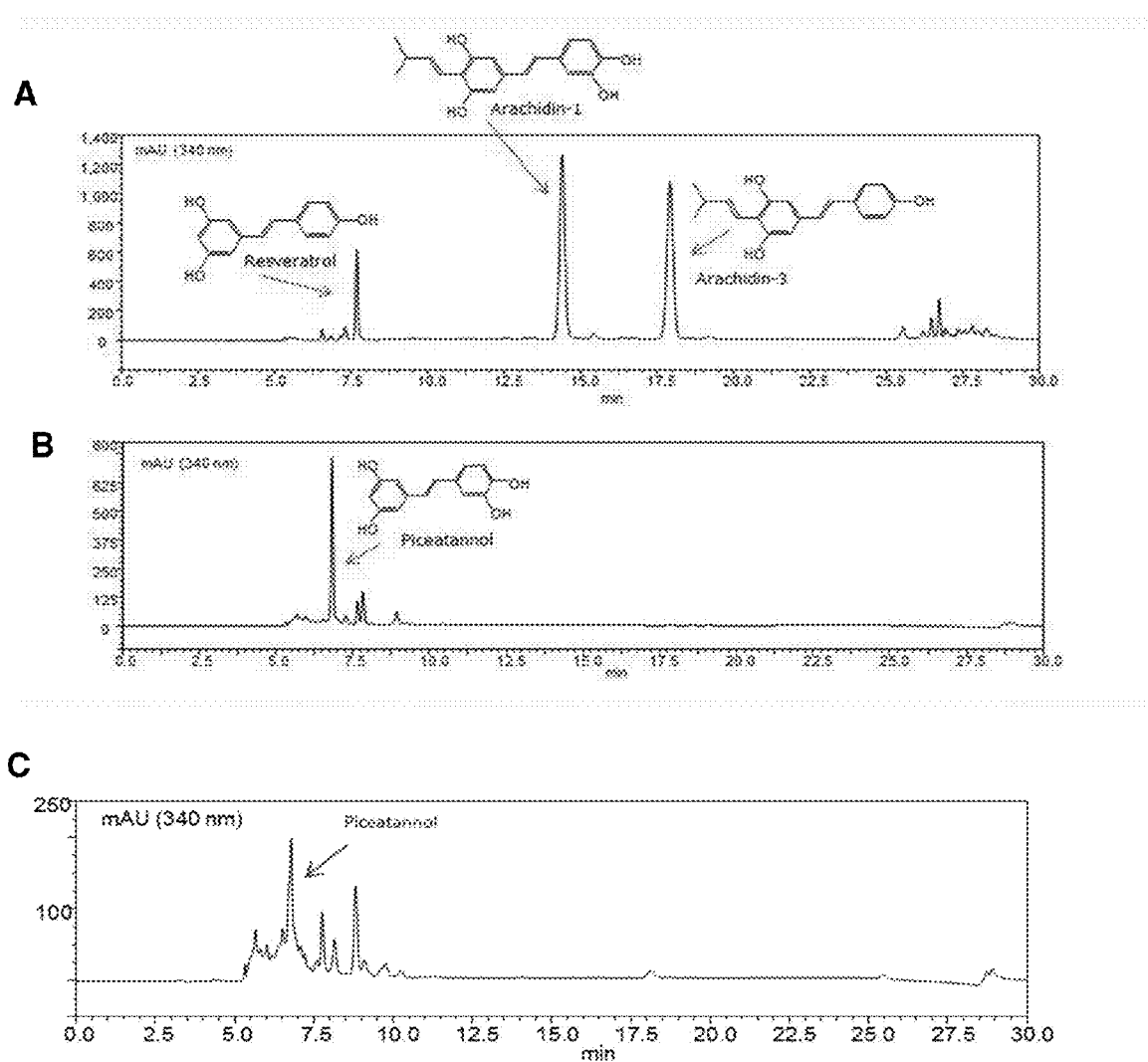
FIG. 6A-C are graphs showing elicitation of stibenoids by sodium acetate (FIG. 6A) and where piceatannol was added (FIG. 6B) and where piceatannol was used alone without sodium acetate (FIG. 6C).

In a first experiment, the effect of piceatannol feeding in sodium acetate treated hairy root cultures of peanut was examined, with results shown in FIGS. 6A and 6B. As can be seen, adding sodium acetate elicitor resulted in production of stilbenoids (resveratrol, arachidin-1 and arachidin-3) in hairy root cultures of plant (FIG. 6A). Adding piceatannol resulted in inhibition of stilbenoid production (FIG. 6B). The impact of inhibition by piceatannol was overcome by adding the trapping agent cyclodextrin, which stopped the feedback inhibition, as seen in FIG. 7A-C. Used alone without an elicitor, no stilbenoids were produced (FIG. 6C).

Figure 7:
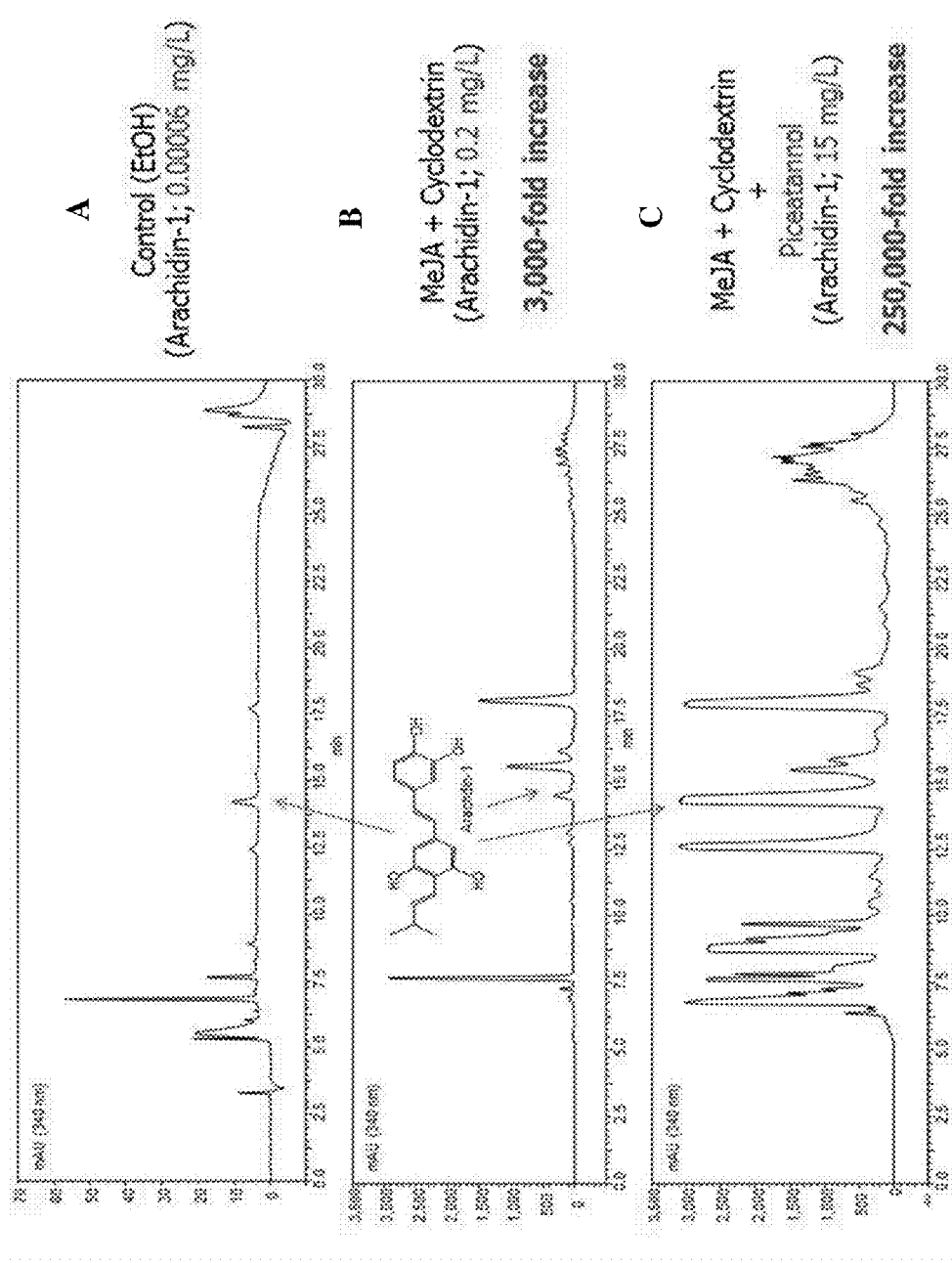
FIG. 7A-C are graphs showing yield of arachidin-1 in control cultures (7A), in cultures treated with cyclodextrin and methyl jasmonate (MeJA) (7B), and in cultures treated with cyclodextrin, MeJA and piceatannol (7C).

FIG. 7 shows the HPLC chromatogram of the stilbenoids at 340 nm (UV max of arachidin-1):

FIG. 7A: Control cultures. The yield of arachidin-1 (peak with retention time of 14.217 minutes) was approximately 0.00006 mg/L;

FIG. 7B: Cultures treated with cyclodextrin and MeJA. The yield of arachidin-1 (peak with retention time of 14.5 minutes) was approximately 0.2 mg/L;

FIG. 7C: Cultures treated with cyclodextrin, MeJA and piceatannol. The yield of arachidin-1 (peak with retention time of 14.35 minutes) was approximately 15 mg/L. Due to the high amount of arachidin-1 in this sample, the extract was diluted before quantitation analysis.

The yield of arachidin-1 was enhanced approximately 250,000 fold in the cultures treated with cyclodextrin, MeJA and piceatannol when compared to control culture. The biosynthetic pathway of arachidin-1 has not been elucidated. Interestingly, in this experiment piceatannol was converted into arachidin-1 suggesting a potential role for piceatannol as a metabolic precursor. An alternative role of piceatannol is as a xenobiotic. In this case, enzymes in the metabolic pathway of arachidin-1 were able to convert piceatannol to arachidin-1. The high levels of arachidin-1 attained in this study indicate a potential role of cyclodextrin in preventing the intrinsic regulatory mechanisms driven by intermediates and products in the arachidin-1 metabolic pathway.

Example 2

Biosynthesis Enhancement of Flavonoids in Hairy Root Cultures of *Scutellaria laterifora*

The genus *Scutellaria* has been widely studied due to its health benefits including, but not limited to, anti-allergic, anti-bacterial, anti-HIV, anti-hepatitis, antioxidant, and anti-tumor activities. Two of the most widely studied species of *Scutellaria* are *S. baicalensis* and *S. laterifora* due to both exhibiting the aforementioned properties and being officially recognized herbal product sources. *S. laterifora* commonly referred to as the American skullcap, has been used for centuries by Europeans and Native Americans as a nerve tonic, sedative, and anticonvulsant. Recent studies have shown that flavonoids present in *S. laterifora* extracts possess strong antitumor properties and therefore these compounds merit further study. In order to study the biosynthesis of the bioactive flavonoids in *S. laterifora* we developed hairy root cultures of this species. Line 4 was selected for further studies based on its growth performance. To manipulate the levels of flavonoids, hairy roots of *S. laterifora* line 4 were cultured for 30 days in a modified Murashige & Skoog medium at 28° C., under shaking (90 rpm) and continuous light. At day 30, the spent medium was removed and the conductivity measured. The spent medium was replaced with fresh medium containing 15 mM of β-cyclodextrin (trapping agent) and 100 µM methyl jasmonate (MeJA, inducer) with a putative precursor (1 mM chrysin or 1 mM naringenin). Control cultures included β-cyclodextrin and MeJA without the putative precursor. Cultures were incubated for additional 24 hours as described above and then the roots and medium were collected. The flavonoids are extracted from the tissue and culture medium with either ethyl acetate or methanol and then the extracts are dried to completeness under nitrogen stream. The extracts are resuspended in methanol and analyzed by reversed phase HPLC. Detection of flavonoids is done with a photodiode array detector. The levels of acteoside, wogonin, wogonoside, baicalein baicalin, scutellarein and scutellarin are determined in extracts from the tissue. In addition, the levels of inducible and secreted compounds are determined in the culture medium.

Figure 8:
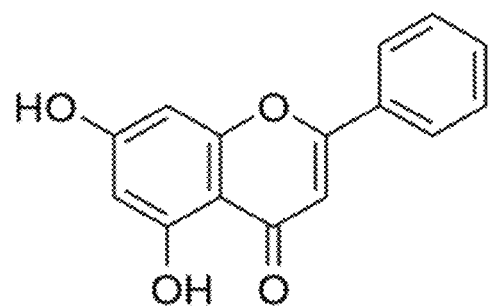
FIG. 8 is a diagram showing the chemical structure of chrysin.
Figure 9:
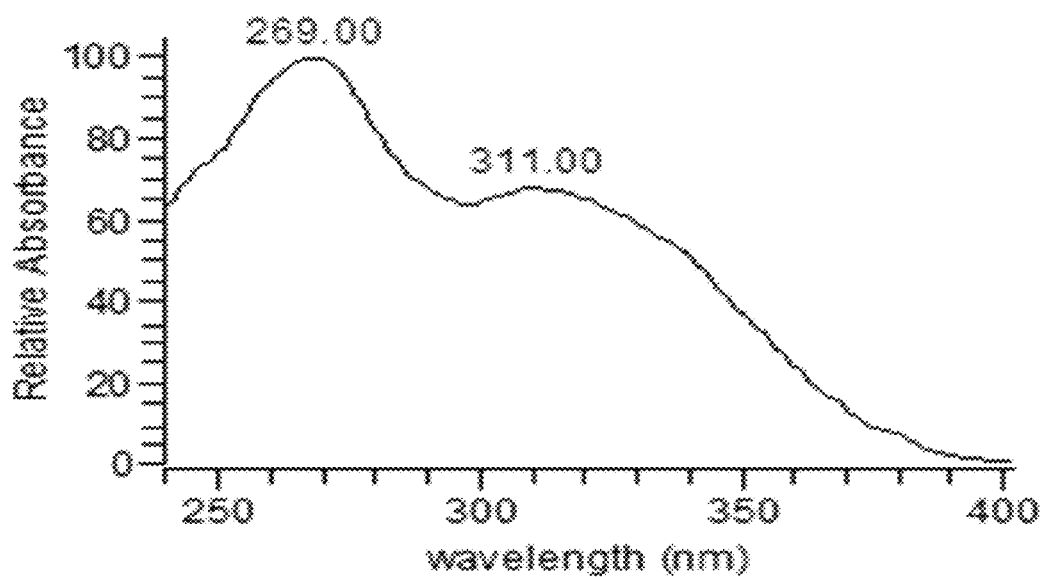
FIG. 9 is a graph showing the UV spectrum of chrysin.
Figure 10:
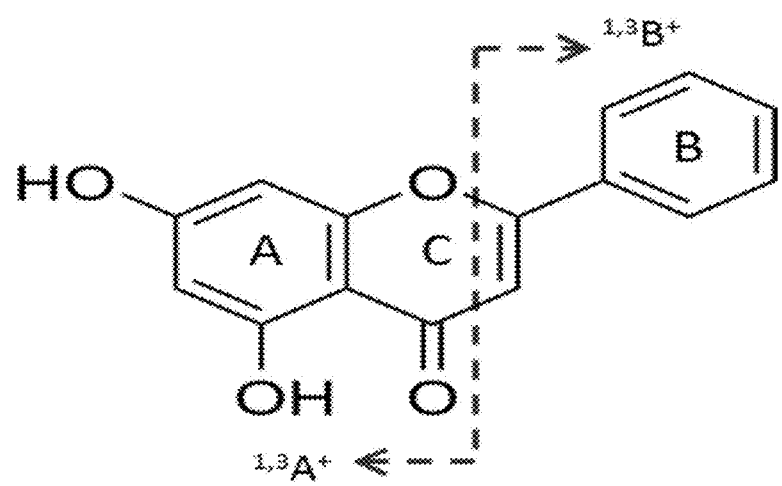
FIG. 10 is a diagram showing the fragmentation pattern of chrysin
Figure 11:
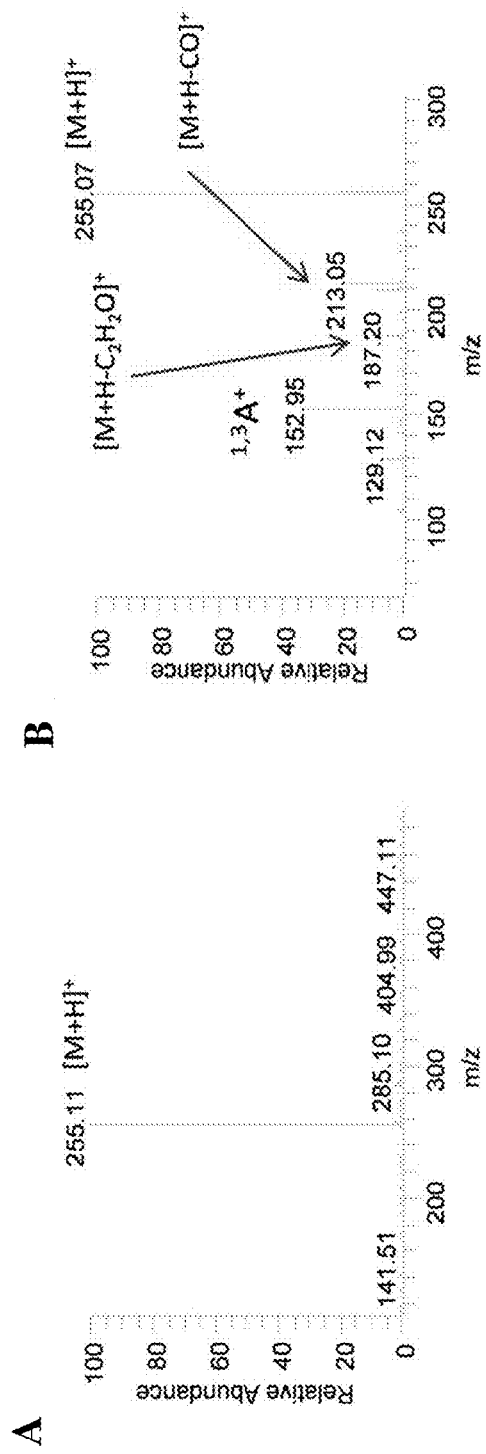
FIG. 11A-B is a graph showing mass spectrometry (MS) spectrum of chrysin (A) and MS2 spectrum of selected ion 255 (B).

Absorption and mass spectrometry analysis of chrysin reference standard is shown in FIGS. 8-21. In FIG. 8, the chemical structure of chrysin is shown, FIG. 9 shows UV spectrum, the fragmentation pattern of chrysin is shown in FIG. 10, and in FIG. 11 mass spectrometry (MS) spectrum of chrysin (A) and MS2 spectrum of selected ion 255 (B) are shown.

Figure 12:
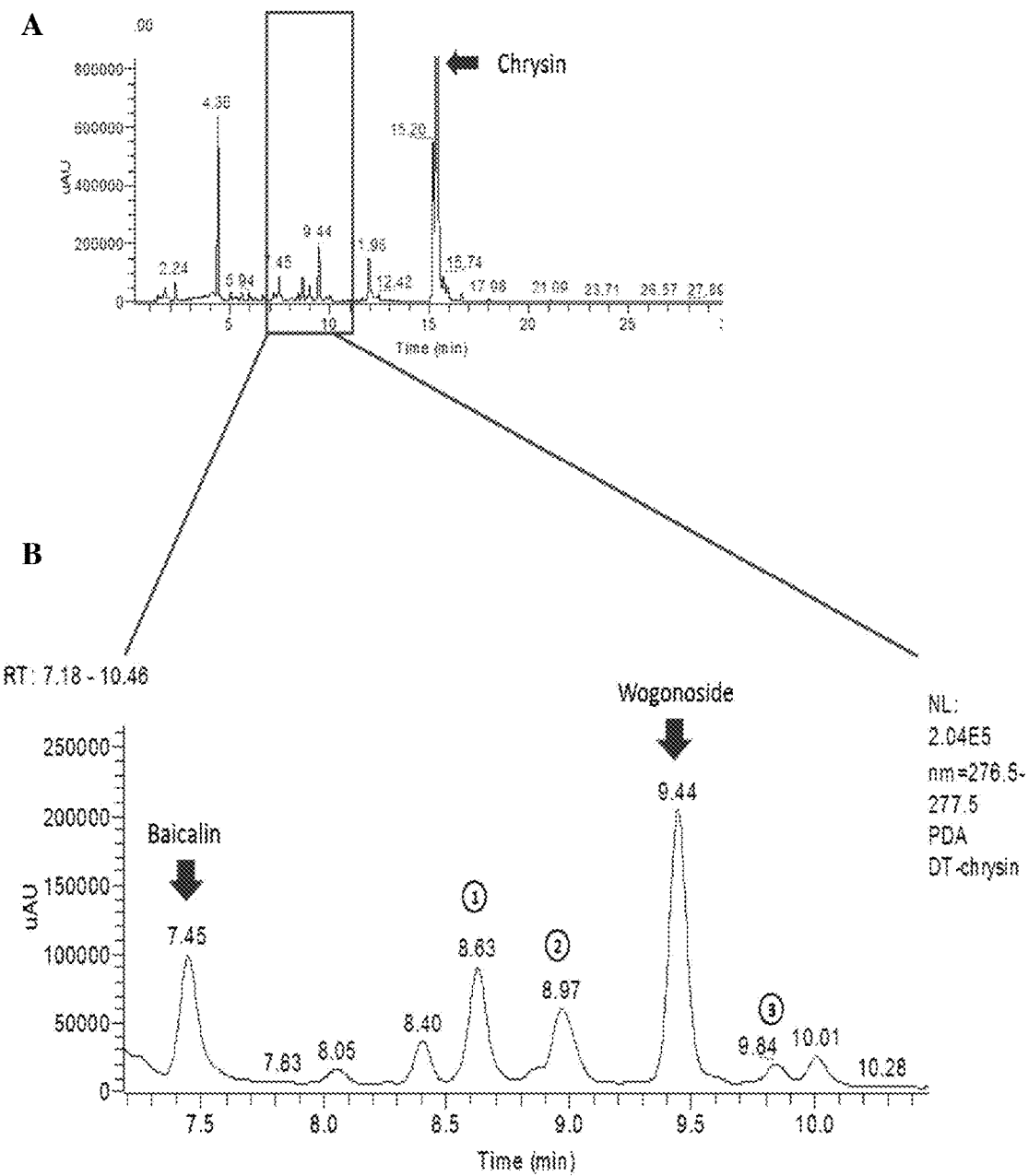
FIGS. 12A-B are graphs showing production of novel chrysin derivatives in 12A and showing increased detail at 12B.

The results of analysis for compounds produced by addition of chrysin is shown in FIG. 12. In FIG. 12A, the peak representing chrysin is identified along with new compounds, shown in detail in FIG. 12B. Novel chrysin derivatives are shown at peaks 1, 2 and 3 produced in the tissue of hairy roots of *S. laterifora*. These cultures were fed with 1 mM chyrsin together with 15 mM cyclodextrin and 100 µM methyl jasmonate. As described above, compounds were extracted with methanol from the lyophilized hairy root tissue and analyzed by HPLC-PDA.

Figure 13:
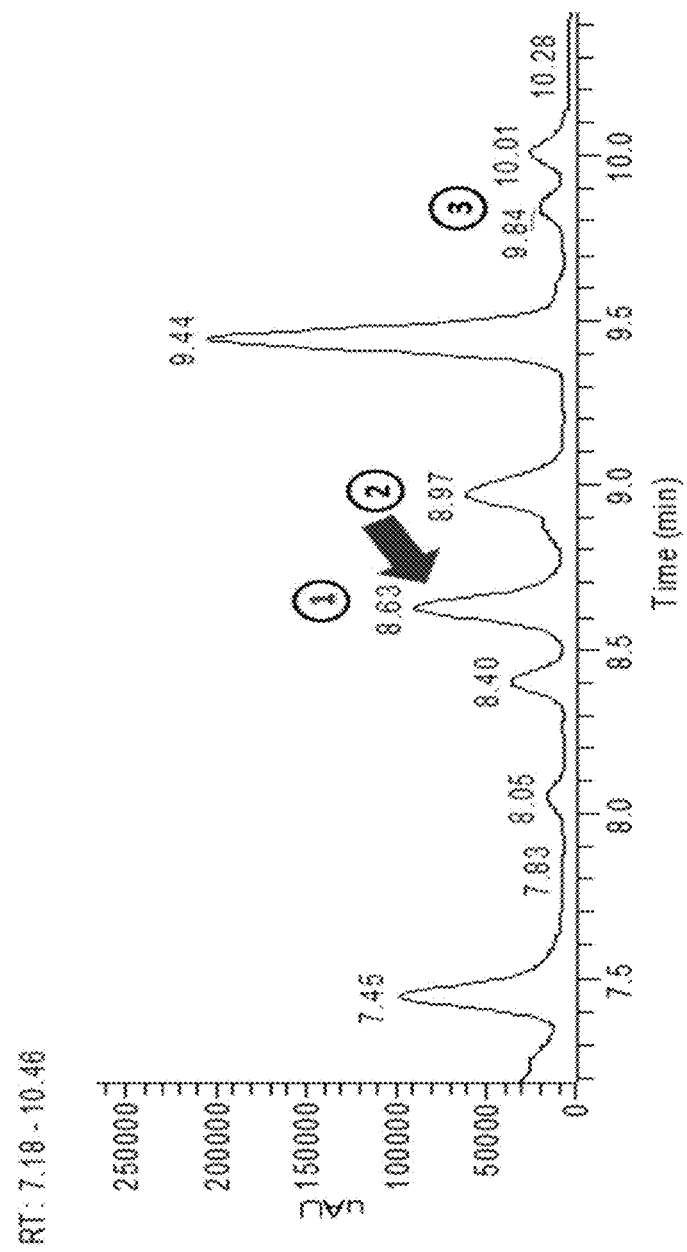
FIG. 13 is a graph showing compounds derived from chrysin with peak 1 identified by arrow and number.
Figure 14:
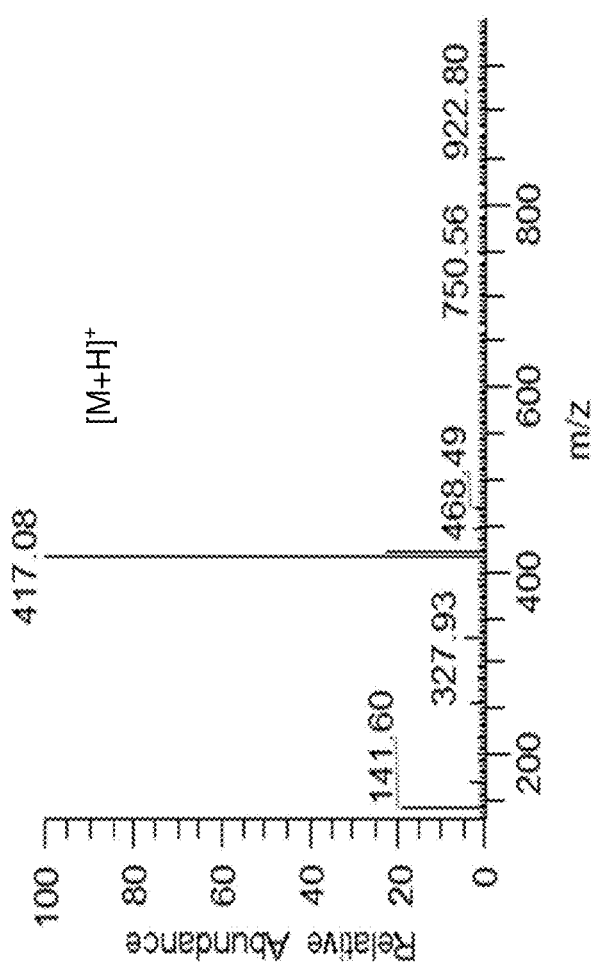
FIG. 14 is a graph showing mass spectrometry analysis of the chrysin glucoside produced in peak 1.
Figure 15:
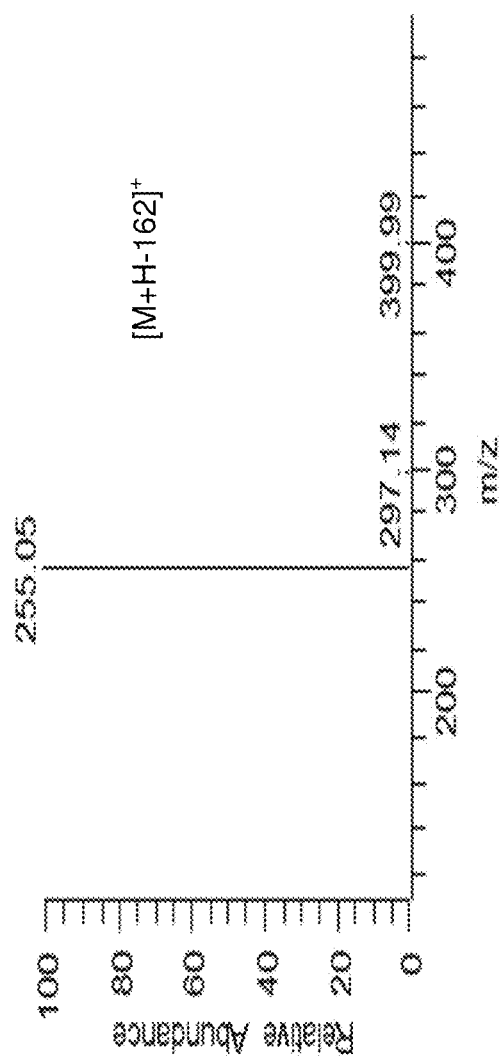
FIG. 15 is a graph showing MS2 spectrum of peak 1.
Figure 16:
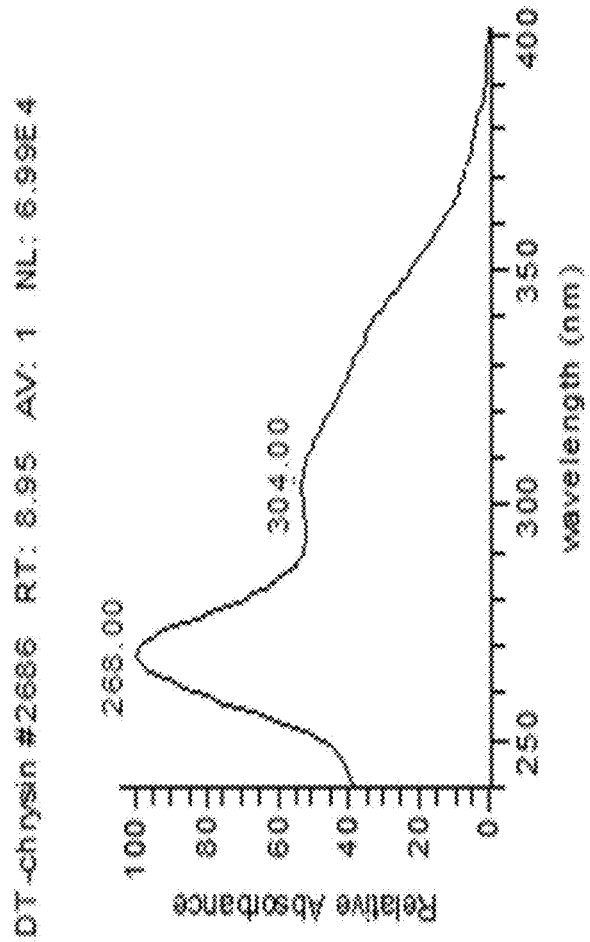
FIG. 16 is a graph showing UV spectrum of peak 1.
Figure 17:
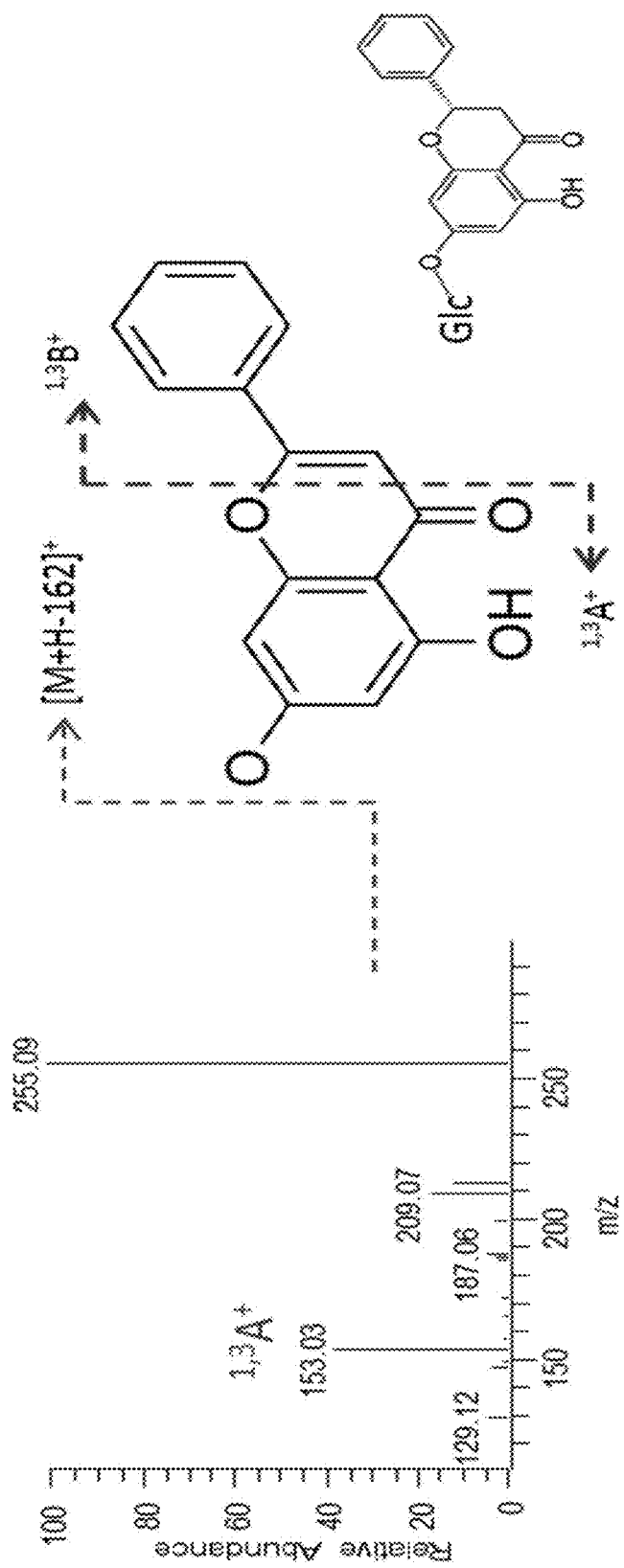
FIG. 17 is a graph showing MS3 spectrum of peak 1 and the predicted fractionation patterns of the compound.

Further analysis of the compound derived from chrysin represented in peak 1 is shown in FIGS. 13-17. FIG. 13 shows absorption and mass spectrometry analysis of chyrsin glucoside, seen as peak 1 (arrow) in FIG. 13. The MS spectrum of peak 1 is shown in the graph of FIG. 14, the MS2 spectrum of peak 1 in FIG. 15 and the UV spectrum in FIG. 16 and MS3 spectrum of peak 1 in FIG. 17 along with the predicted fractionation patterns of the compound.

Figure 18:
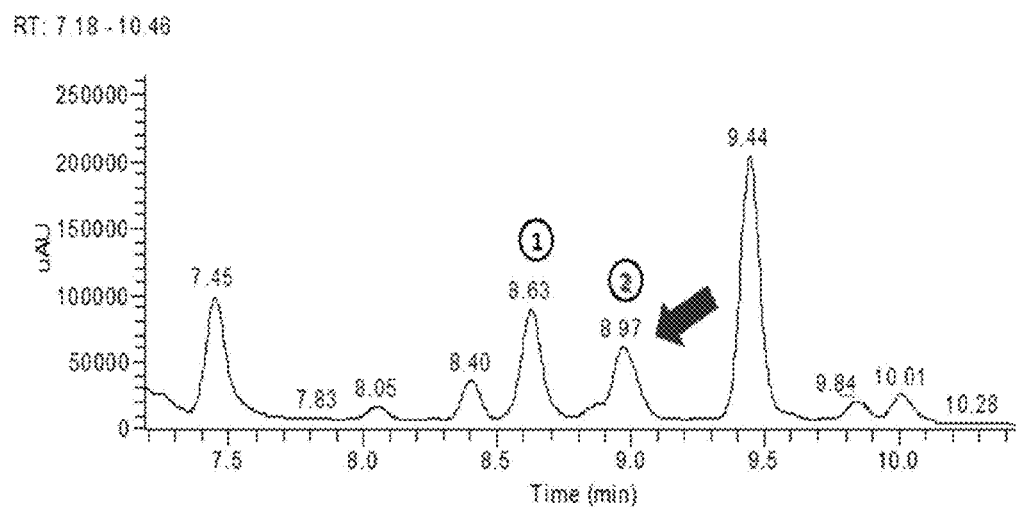
FIG. 18 is a graph showing compounds derived from chrysin with peak 2 identified by arrow and number.
Figure 19:
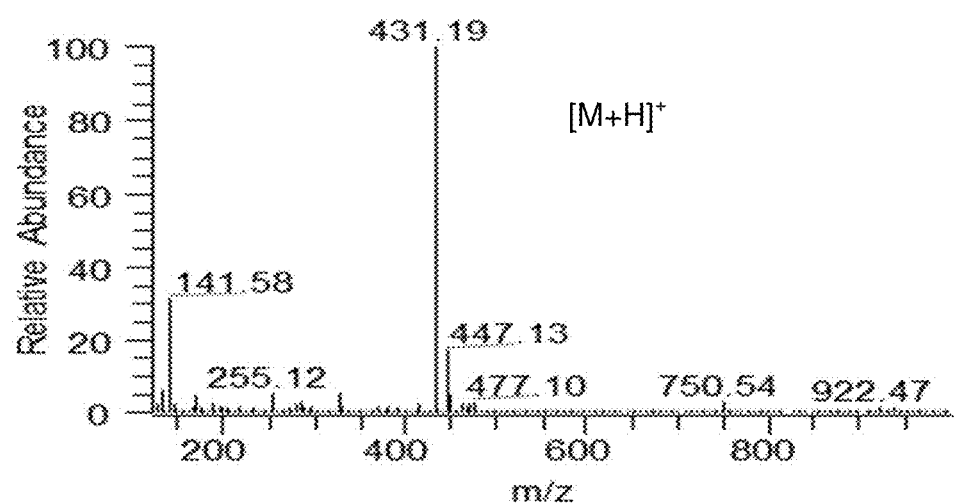
FIG. 19 is a graph showing mass spectrometry analysis of the chrysin glucuronide produced in peak 2.
Figure 20:
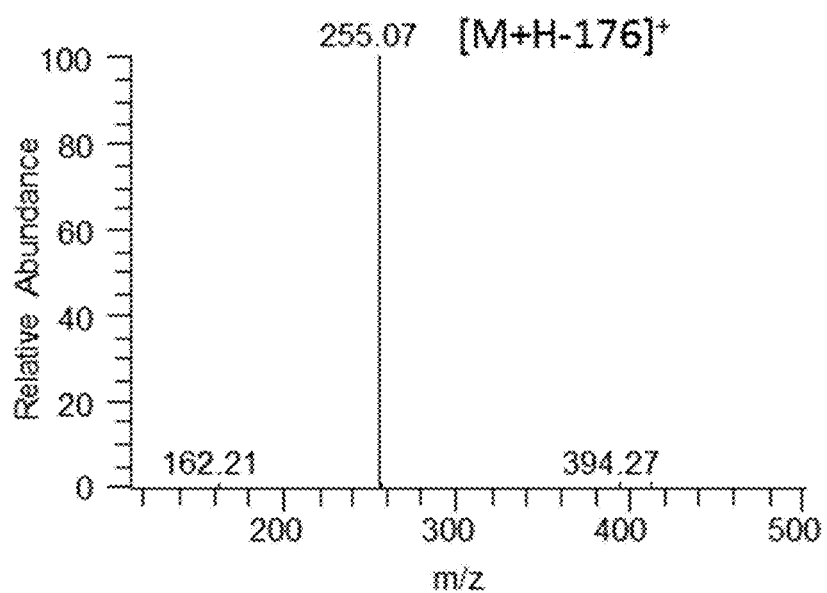
FIG. 20 is a graph showing MS2 spectrum of peak 2.
Figure 21:
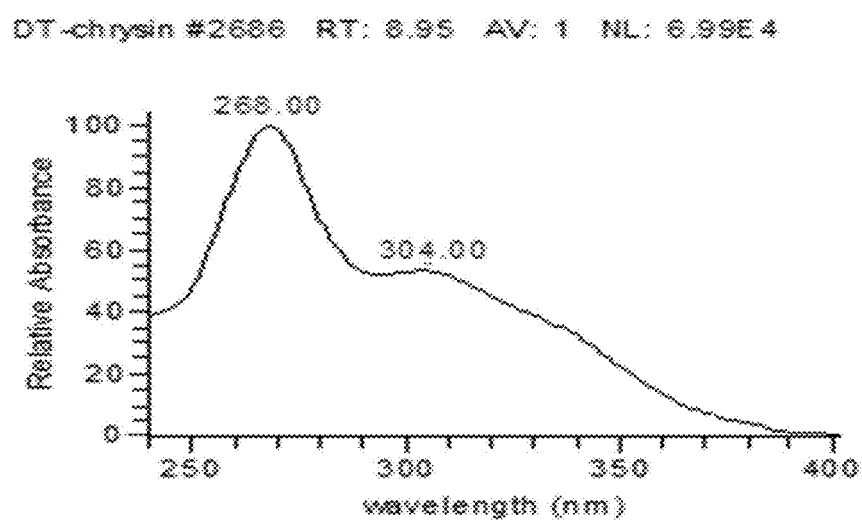
FIG. 21 is a graph showing UV spectrum of peak 2.
Figure 22:
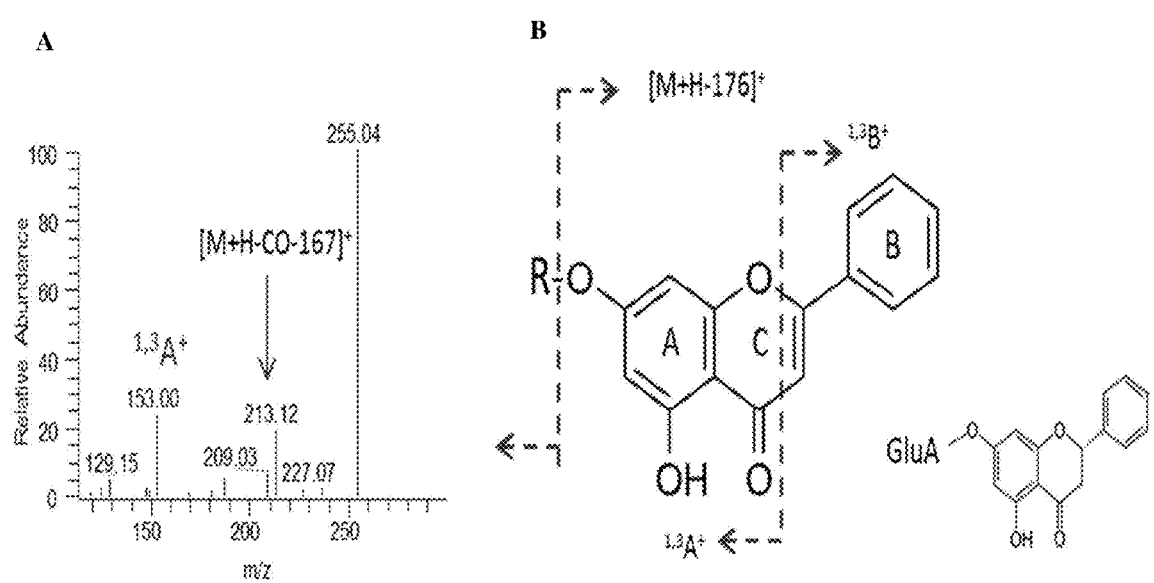
FIG. 22A is a graph showing MS3 spectrum of peak 2 and FIG. 22B the predicted fractionation patterns of the compound.

Peak 2 as identified in FIG. 18 by arrow is a chrysin glucuronide produced and further analysed. FIG. 19 shows the MS spectrum of peak 2, FIG. 20 shows MS2 spectrum and FIG. 21 shows the UV spectrum and FIG. 22A the MS3 spectrum and FIG. 22B the predicted fractionation pattern of the compound.

Figure 23:
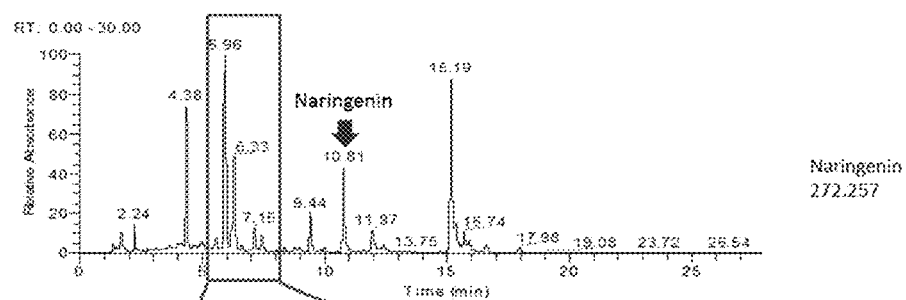
FIG. 23A-B are graphs showing production of novel naringenin derivatives in 23A and showing increased detail at 23B.
Figure 23:
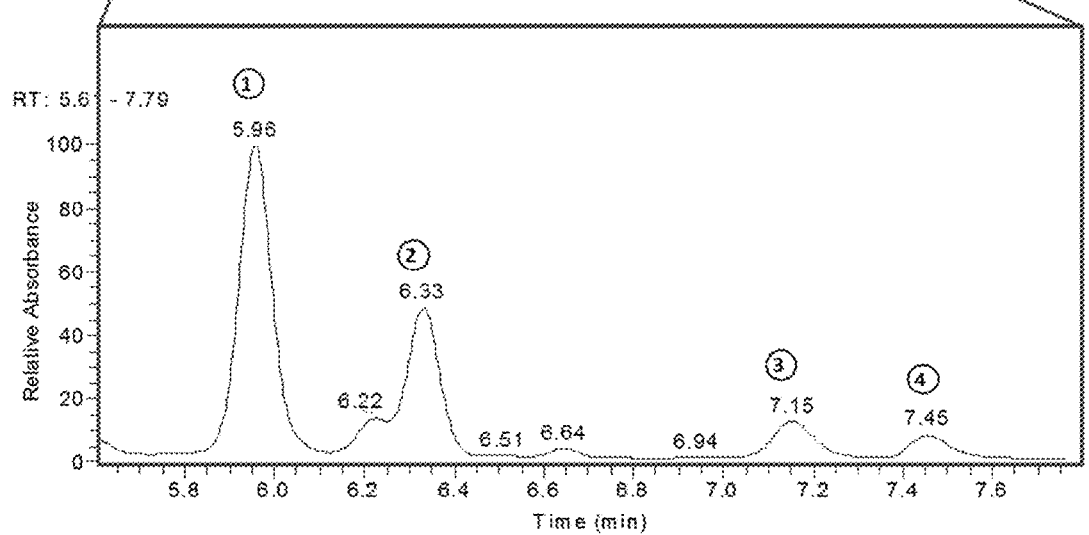
Figure 24:
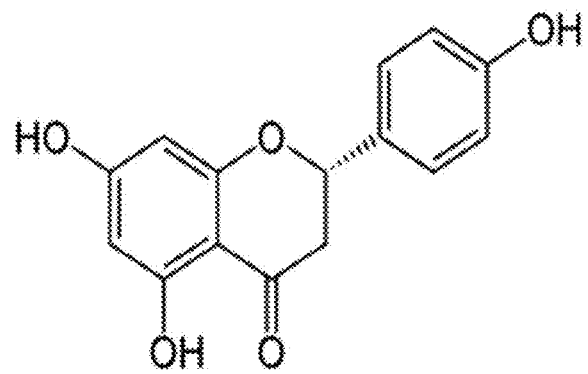
FIG. 24 shows the chemical structure of naringenin.
Figure 25:
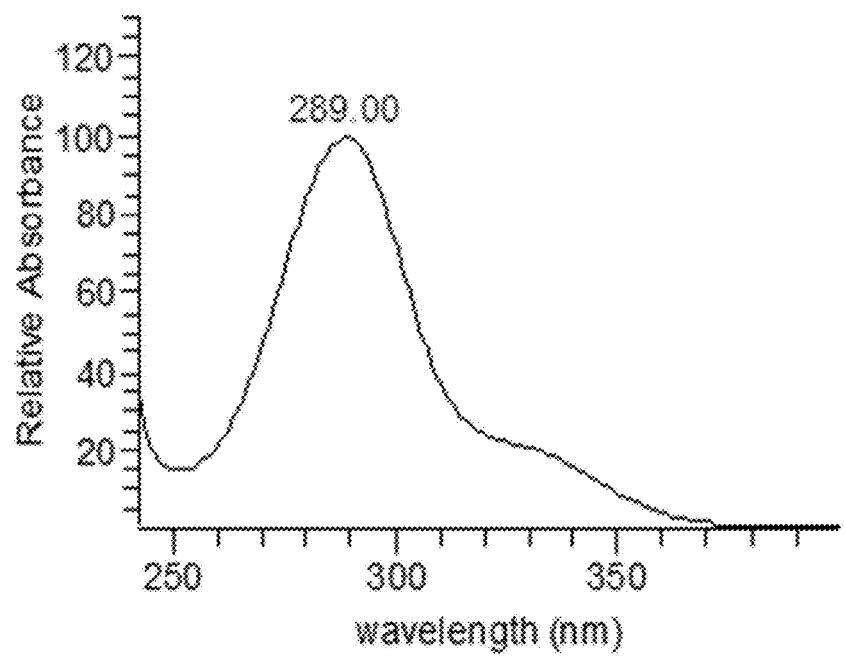
FIG. 25 is a graph showing the UV spectrum of naringenin.

Using another precursor, narigenin, still further new narigenin derivatives were produced in the tissue of hairy root cultures of *S. lateriflora*, as reflected in FIG. 23. FIG. 23A shows the identification of naringenin, and detail of four derivatives seen at peaks 1-4 shown in FIG. 23B. These compounds were extracted with methanol from the lyophilized hairy root tissue and analyzed by HPLC-PDA. The chemical structure of naringenin is shown in FIG. 24 and a graph showing the UV spectrum of naringenin in FIG. 25.

Figure 26:
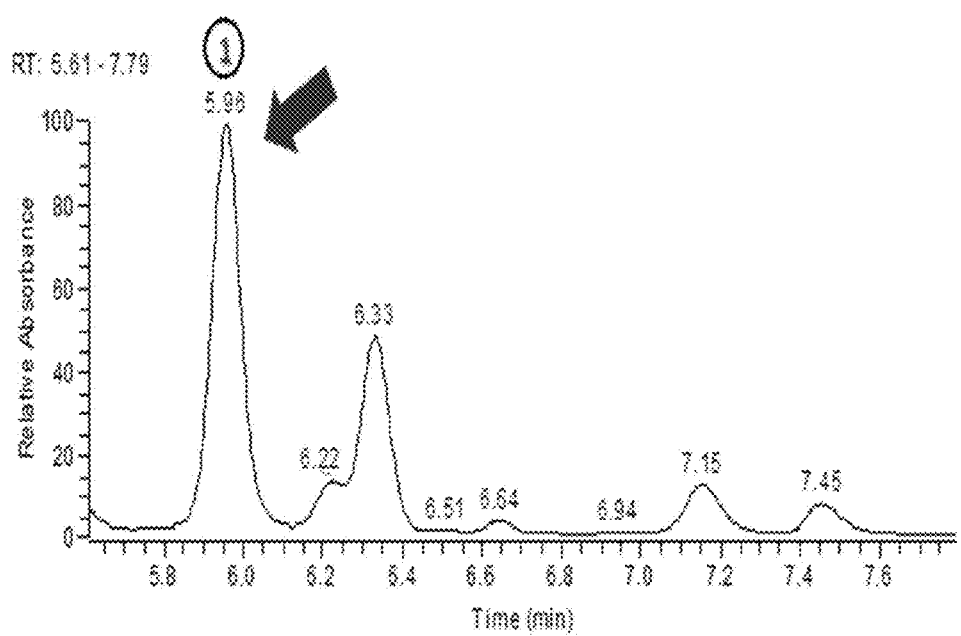
FIG. 26 is a graph showing compounds derived from naringenin with peak 1 identified by arrow and number.
Figure 27:
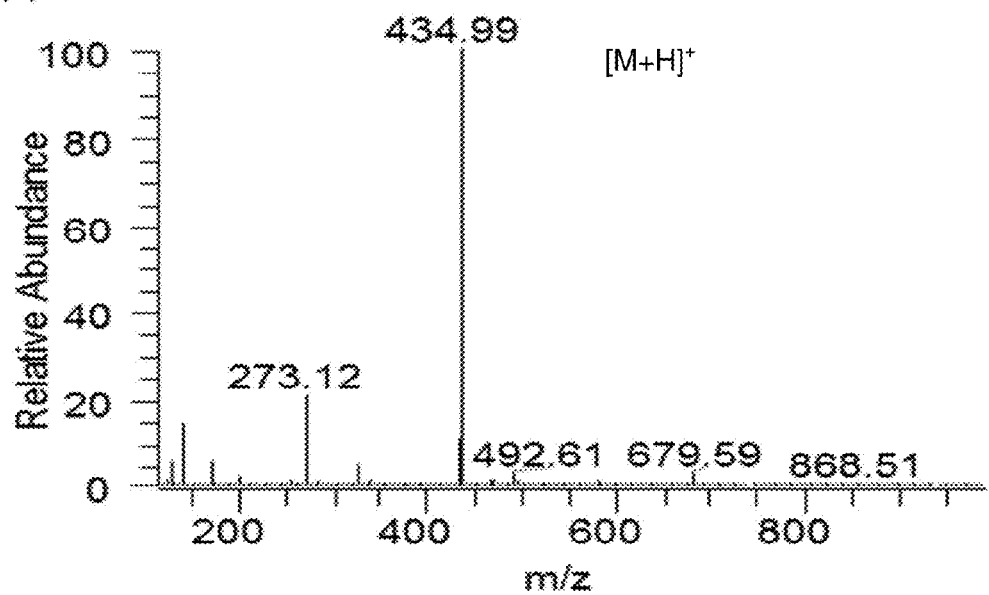
FIG. 27 is a graph showing MS spectrum of peak 1.
Figure 28:
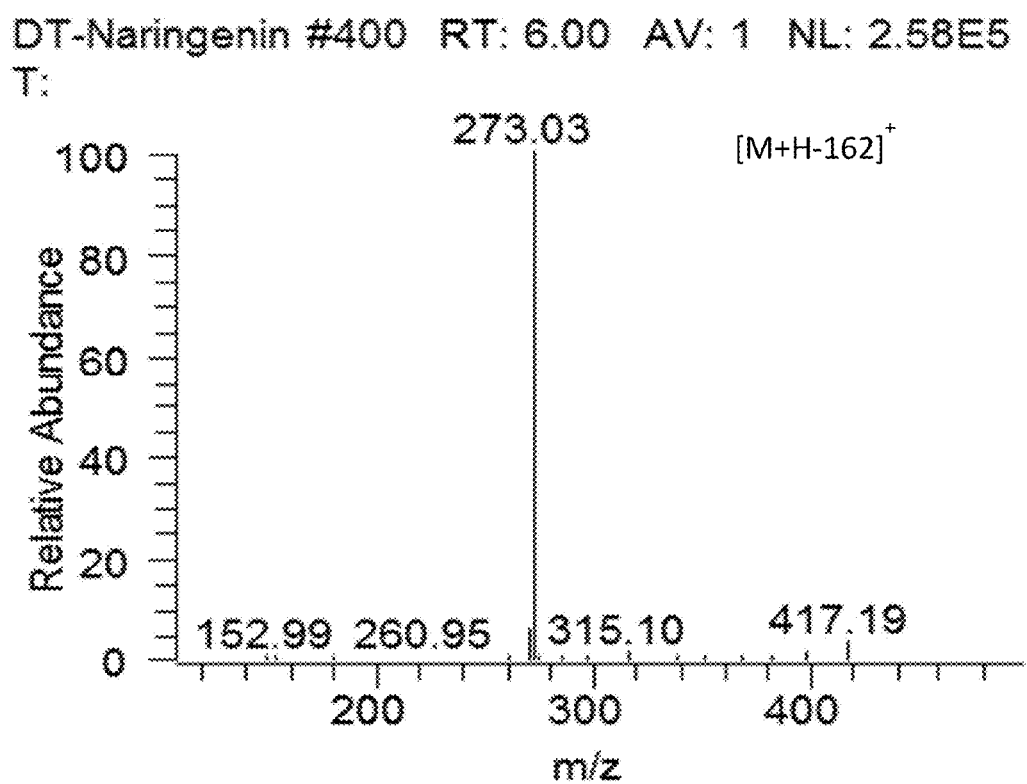
FIG. 28 is a graph showing MS2 spectrum of peak 1.
Figure 29:
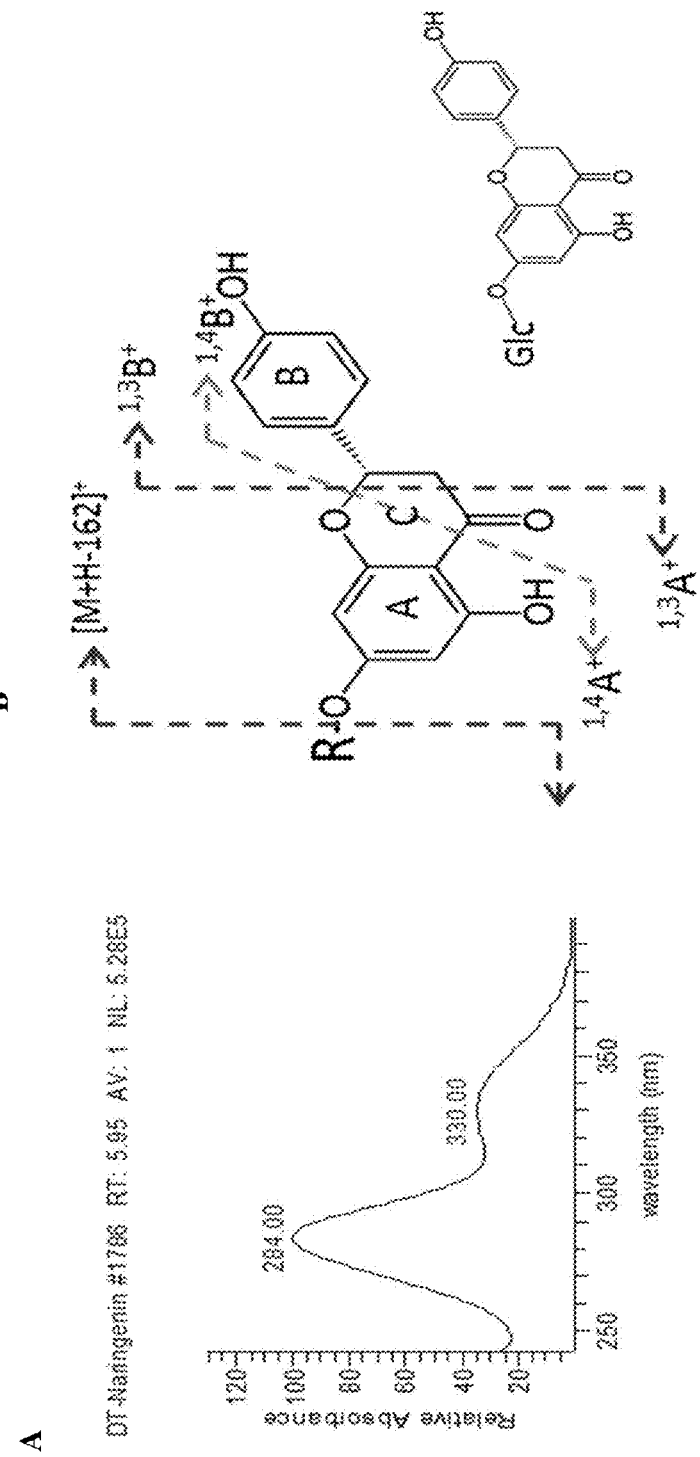
FIG. 29A is a graph showing the UV spectrum of peak 1 and FIG. 29 B shows the predicted fractionation patterns of the compound.
Figure 30:
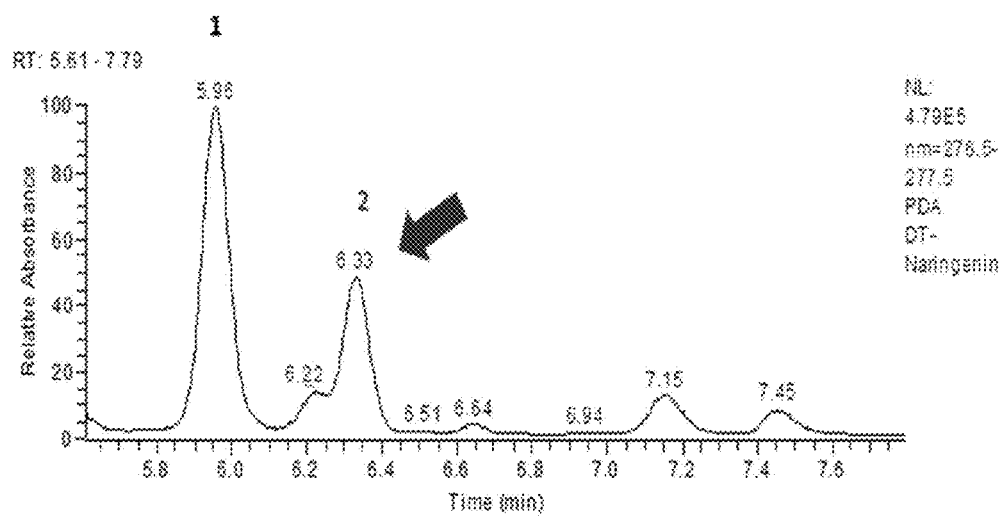
FIG. 30 is a graph showing compounds derived from naringenin with peak 2 identified by arrow and number.
Figure 31:
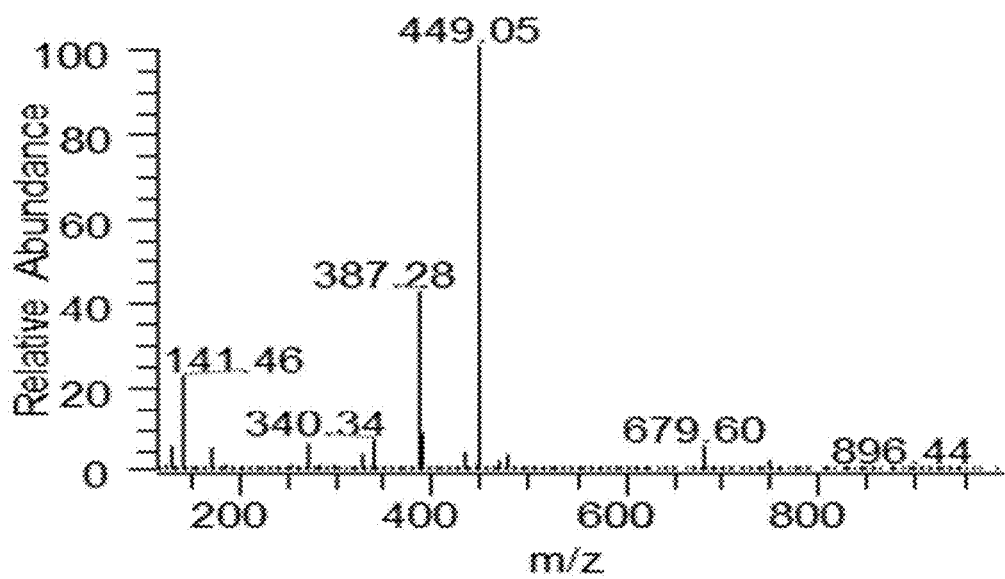
FIG. 31 is a graph showing MS spectrum of peak 2.
Figure 32:
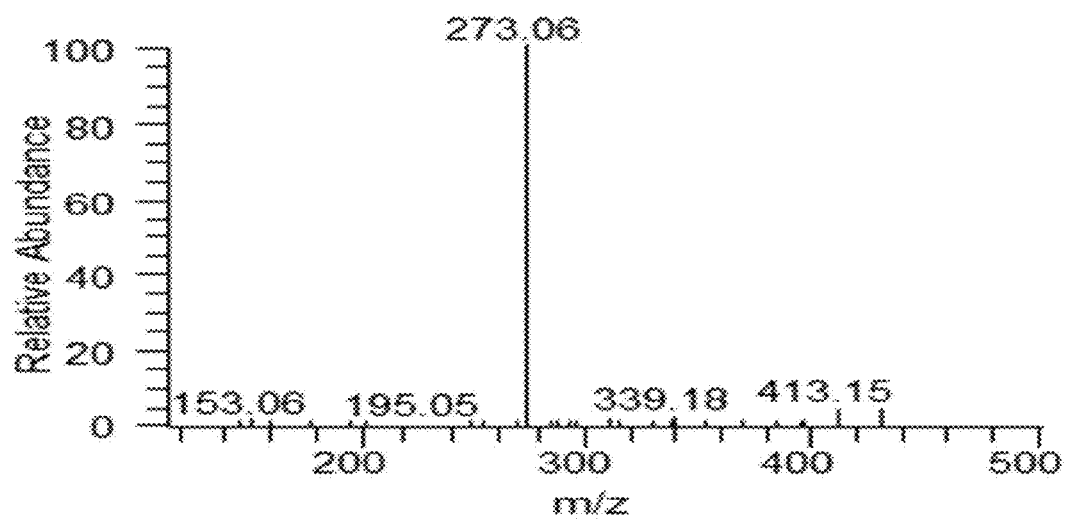
FIG. 32 is a graph showing MS2 spectrum of peak 2.
Figure 33:
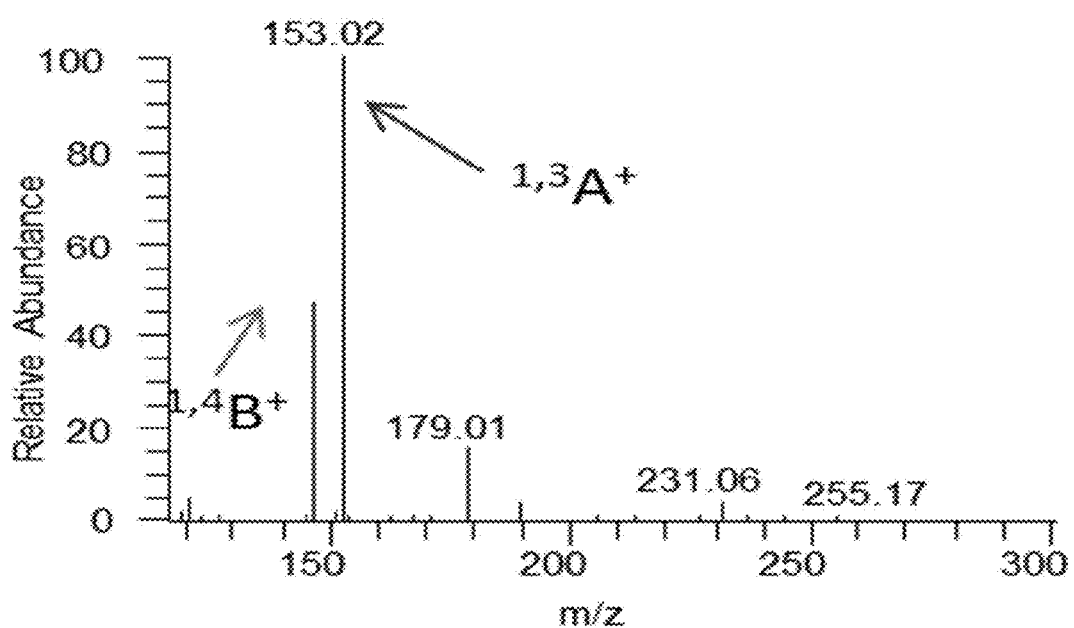
FIG. 33 is a graph showing MS3 spectrum of peak 2.
Figure 34:
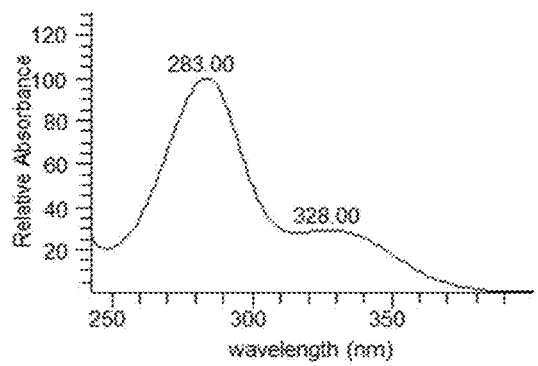
FIG. 34A is a graph showing the UV spectrum of peak 2 and FIG. 34 B shows the predicted fractionation patterns of the compound.
Figure 34:
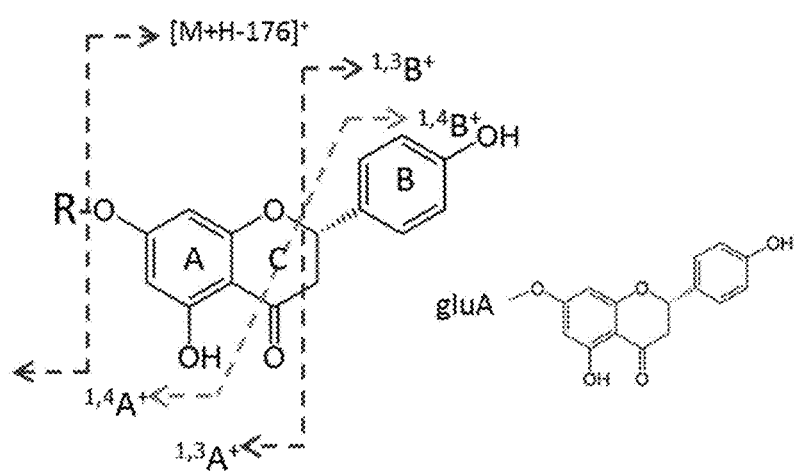

Further analysis of the compound derived from naringenin represented in peak 1 is shown in FIGS. 26-34. FIG. 26 shows absorption and mass spectrometry analysis of naringenin glucoside, seen as peak 1 (arrow). The MS spectrum of peak 1 is shown in the graph of FIG. 27, the MS2 spectrum of peak 1 in FIG. 28 and the UV spectrum in FIG. 29A along with the predicted fractionation patterns of the compound shown in FIG. 29B. In FIG. 30 absorption and mass spectrometry analysis of naringenin glucuronic acid is seen as peak 2 (arrow). The MS spectrum of peak 2 is shown in the graph of FIG. 31, the MS2 spectrum of peak 2 in FIG. 32, MS3 spectrum of peak 2 in FIG. 33 and UV spectrum in FIG. 34A along with the predicted fractionation patterns of the compound shown in FIG. 34B.

Thus use of the elicitor with a trapping agent and precursor produces new compounds of value. Particularly useful are those which add a carbohydrate to the moiety. Compounds produced include glucosides as well as glucuronides. Glucuronidation is important for drug metabolism in humans and to date there are no efficient means to make these compounds. In a representative example here, hairy roots were treated with precursor chrysin or naringenin, trapping agent cyclodextrin and an elicitor to produce chrysin glucoside and chrysin glucuronide, as well as naringenin glucoside and naringenin glucuronide and other novel compounds, as confirmed by UV and MS analysis. The process thus can produce valuable biological compounds that do not otherwise have efficient means of production.

Continued tracking of production of the product of interest shows amount of the product continued to increase over at least a 90 hours period.

Example 3

Biosynthesis Enhancement of Steroidal Alkaloids in Cell Suspension Cultures of *Veratrum californicum*

*Veratrum californium* is the only source of the potent anticancer alkaloid cyclopamine. Due to the complex chemical structure of this steroidal alkaloid its production through chemical synthesis is not commercially feasible. In efforts to develop a sustainable bioproduction system for cyclopamine and related steroidal alkaloids we developed cell suspension and adventitious root cultures of *V. californicum*. We demonstrated by HPLC and mass spectrometry analyses that several important steroidal alkaloids including cyclopamine, cycloposine, veratromine and veratrosine can be produced by these plant cultures. In order to increase the levels of these compounds we are treating cell suspension cultures of *V. californicum* with squalene (a biosynthetic precursor), cyclodextrin and methyl jasmonate.

Cell suspension cultures of *V. californium* are maintained in a modified MS medium under constant shaking under darkness at 24° C. At a specific stage of development, the spent medium is being removed and replaced with fresh medium containing 15 mM of β-cyclodextrin (trapping agent) and 100 µM methyl jasmonate (MeJA, inducer) with or without 1 mM squalene. Cultures are incubated for additional 24 hours as described above and then the cells and medium are collected. The steroidal alkaloids are extracted from the cells with methanol and from the culture medium with dichloromethane. The extracts are dried to completeness under nitrogen stream, resuspended in methanol and analyzed by reversed phase HPLC coupled with an ion-trap mass spectrometer. Detection and quantitation of the steroidal alkaloids is done by mass spectrometry.

REFERENCES

Aggarwal, B. B., Bhardwaj, A., Aggarwal, R. S., Seeram, N. P., Shishodia, S., and Takada, Y. (2004) Role of Resveratrol in Prevention and Therapy of Cancer: Preclinical and Clinical Studies. Anticancer Res. 24:1-60.

Babu S K, Kumar K V, Subbaraju G V (2005) Estimation of trans-resveratrol in herbal extracts and dosage forms by high-performance thin-layer chromatography. Chem Pharm Bull 53:691-693. DOI 10.1248/cpb.53.691

Baur J, Sinclair D A (2006) Therapeutic potential of resveratrol: the in vivo evidence. Nat Rev Drug Discov. 5:493-506

Becker J, Armstrong G O, van der Merwe M J, Lambrechts M J, Vivier M A, Pretorius I S (2003) Metabolic engineering of *Saccharomyces cerevisiae* for the synthesis of the wine-related antioxidant resveratrol. FEMS Yeast Res 4:79-85.

Bru R, Selles S, Casado-Vela J, Belchi-Navarro S, Pedreno M A (2006) Modified cyclodextrins are chemically defined glucan inducers of defense responses in grapevine cell cultures. J Agri Food Chem. 54-65-71

Camilleri, C., Jouanin, L., 1991. The TR-DNA region carrying the auxin synthesis genes of the *Agrobacterium rhizogenes* agropine-type plasmid pRiA4: nucleotide sequence analysis and introduction into tobacco plants. Mol. Plant Microbe Interact. 4, 155-162.

Caspeta L, Quintero R, Villarreal M L (2005) Novel airlift reactor fitting for hairy root cultures: developmental and performance studies. Biotechnol Prog. 21:735-740

Celimene C, Micales J, Ferge L, Young R (1999) A. Efficacy of pinosylvins against white-rot and brown-rot fungi. Holzforschung. 53: 491-497

Chen R S, Wu P L, Chiou R Y (2002) Peanut roots as a source of resveratrol. J Agric Food Chem. 50:1665-1667

Chang, J.-C., Lai, Y.-H., Djoko, B., Wu, P.-L., Liu, C.-D., Liu, Y.-W., and Chiou, R., Y-Y. (2006) Biosynthesis enhancement and antioxidant and anti-inflammatory activities of peanut arachidin-1, arachidin-3, and isopentadienylresveratrol. J. Agric. Food Chem. 54:10281-10287.

Chung I M, Park M R, Rehman S, Yun S J (2001) Tissue specific and inducible expression of resveratrol synthase gene in peanut plants. Mol Cells 12:353-359

Condori J, Medina-Bolivar F (2006) *Agrobacterium rhizogenes* strain ATCC 15834 plasmid pRi 15834 3-indoleacetamide hydrolase (aux2) and trytophan 2-monooxygenase (aux1) genes, complete cds. NCBI Accession No. DQ782955

Delmas D, Lancon A, Colin D, Jannin B, Latruffe N (2006) Resveratrol as a chemopreventive agent: a promising molecule for fighting cancer. Curr Drug Targets 7:423-442

Frankel E, Waterhouse A, Kinsella J (1993) Inhibition of human LDL oxidation by resveratrol. Lancet. 341:1103-1104.

Gamborg O L, Miller R A, Ojima K (1968) Nutrient requirements of suspension cultures of soybean root cells. Exp Cell Res 50:151-158

Gehm B D, McAndrews J M, Chien P Y, Jameson J L (1997) Resveratrol, a polyphenolic compound found in grapes and wine, is an agonist for the estrogen receptor. Proc Natl Acad Sci 94:14138-14143

Guillon S, Tremouillaux-Guiller J, Pati P K, Rideau M, Gantet P (2006) Hairy root research: recent scenario and exciting prospects. Curr Opi Plant Biol. 9:341-346

Hall D, De Luca V (2007) Mesocarp localization of a bi-functional resveratrol/hydroxycinnamic acid glucosyltransferase of Concord grape (*Vitis labrusca*). Plant J 49: 579-591.

Holsters M, de Waele D, Depicker A, Messens E, van Montagu M, Schell J (1998) Transfection and transformation of *Agrobacterium tumefaciens*. Mol Gen Genet. 163-181-187.

Huang Y, Tsai W, Shen C, Chen C (2005) Resveratrol derivatives from the roots of *Vitis thunbergii*. J Nat Prod 68: 217-220

Jeandet P, Douillet-Breuil A C, Bessis R, Debord S, Sbaghi M, Adrian M. (2002) Phytoalexins from the Vitaceae: biosynthesis, phytoalexin gene expression in transgenic plants, antifungal activity, and metabolism. J. Agric. Food. Chem. 50:2731-41.

Komarnytsky S, Gaume A, Garvey A, Borisjuk N, Raskin I (2004) A quick and efficient system for antibiotic-free expression of heterologous genes in tobacco roots. Plant Cell Rep. 22: 765-773

Kopp P (1998) Resveratrol, a phytoestrogen found in red wine. A possible explanation for the conundrum of the 'French paradox'? Eur J Endocrinol. 138:619-620

Larronde F, Richard T, Delaunay J C, Decendit A, Monti J P, Krisa S, Mérillon J M (2005) New stilbenoid glucosides isolated from *Vitis vinifera* cell suspension cultures (cv. Cabernet Sauvignon). Planta Med 71:888-890. DOI 10.1055/s-2005-871294

Lee J, Jung E, Lim J, Lee J, Hur S, Kim S S, Lim S, Hyun C G, Kim Y S, Park D. (2006) Involvement of nuclear factor-kappaB in the inhibition of pro-inflammatory mediators by pinosylvin. Planta Med. 72:801-806.

Medina-Bolivar F, Wright R, Funk V, Sentz D, Barroso L, Wilkins T, Petri Jr. W, Cramer C (2003) A non-toxic lectin for antigen delivery of plant-based mucosal vaccines. Vaccine 21:997-1005

Medina-Bolivar F, Cramer C (2004) Production of recombinant proteins in hairy roots cultured in plastic sleeve bioreactors In: Balbas P, Lorence A (eds) Recombinant gene expression: Reviews and protocols. Humana Press, Totowa, pp 351-363

Mikstacka, R., Rimando, A. M., Szalaty, K., Stasik, K., and Baer-Dubowska, W. (2006) "Effect of natural analogues of trans-resveratrol on cytochromes P4501A2 and 2E1 catalytic activities". Xenobiotica, 36: 269-285.

Miura D, Miura Y, Yagasaki K (2003) Hypolipidemic action of dietary resveratrol, a phytoalexin in grapes and red wine, in hepatoma-bearing rats. Life Sciences 73:1393-1400. DOI 10.1016/S0024-3205(03)00469-7 http://dx.doi.org/10.1016/50024-3205%2803%2900469-7

Nepote V, Grosso N R, Guzman C A (2004) Radical scavenging activity of extracts of argentine peanut skins (*Arachis hypogaea*) in relation to its trans-resveratrol content. J Argent Chem Soc 92:41-49

Nopo-Olazabal L, Woffenden B, Reed D, Buswell S, Zhang C, Medina-Bolivar F. Differential expression of the "super-promoter" in leaves and hairy roots of tobacco. 2005 In Vitro Biology Meeting, Abstract P-2037

Orallo F (2006) Comparative studies of the antioxidant effects of cis- and trans-resveratrol. Curr Med Chem. 13:87-98

Park E J, Min H Y, Ahn Y H, Bae C M, Pyee J H, Lee S K. (2004) Synthesis and inhibitory effects of pinosylvin derivatives on prostaglandin E2 production in lipopolysaccharide-induced mouse macrophage cells. Bioorg Med Chem Lett. 14:5895-5898.

Pitta-Alvarez, S., Giulietti, A., 1999. Influence of chitosan, acetic acid and citric acid on growth and tropane alkaloid production in transformed roots of *Brugmansia candida* Effect of medium pH and growth phase. Plant Cell Tissue Org. Cult. 59, 31-38.

Ramakrishnan D, Curtis W R (2004) Trickle-bed root culture bioreactor design and scale-up: growth, fluid-dynamics, and oxygen mass transfer. Biotechnol. Bioeng. 88:248-260.

Rimando A M, Barney D L (2005) Resveratrol and naturally occurring analogues in *Vaccinium* species. Acta Horticulture Proceedings 6:137-143

Rimando A M, Nagmani R, Feller D R, Yokoyama W (2005) Pterostilbene, a new agonist for the peroxisome proliferator-activated receptor α-isoform, lowers plasma lipoproteins and cholesterol in hypercholesterolemic hamsters. J Agric Food Chem 53:3403-3407

Roupe, K., Remsberg, C., Yanez, J., Davies, N., 2006a. Pharmacometrics of stilbenes: seguing towards the clinic. Curr. Clin. Pharm. 1, 81-101.

Roupe, K., Yanez, J., Teng, X. W., and Davies, N., 2006b. Pharmacometrics of selected stilbenes: srhapontigenin, piceatannol, pinosylvin. J. Pharm. Pharmacol. 58, 1443-1450.

Rudolf J R, Resurreccion A V (2005) Elicitation of resveratrol in peanut kernels by application of abiotic stresses. J Agric Food Chem 53:10186-10192. DOI 10.1021/jf0506737

Savary B, Flores H (1994) Biosynthesis of defense-related proteins in transformed root cultures of *Trichosanthes kirilowii* Maxim. var *japonicum* (Kitam.). Plant Physiol 106:1195-1204

Schmülling, T., Schell, J., Spena, A., 1988. Single genes from *Agrobacterium rhizogenes* influence plant development. EMBO J. 7, 2621-2629.

Slightom, J. L., Durand-Tardif, M., Jouanin, L., Tepfer, D., 1986. Nucleotide sequence analysis of TL-DNA of *Agrobacterium rhizogenes* agropine type plasmid. Identification of open reading frames. J. Biol. Chem. 261, 108-121.

Soleas G J, Angelini M, Grass L, Diamandis E P & Goldberg D M. (2001) Absorption of trans-resveratrol in rats. Methods Enzymol., 335:145.

Tabata Y, Takano K, Ito T, Iinuma M, Yoshimoto T, Miura H, Kitao Y, Ogawa S, Hori O. (2007) "Vaticanol B, a resveratrol tetramer, regulates endoplasmic reticulum (ER) stress and inflammation." Am J Physiol Cell Physiol. E-Published; doi:10.1152/ajpcell.00095.2007

Tassoni A, Formnlè S, Franceschetti M, Musiani F, Michael A J, Perry B, Bagni N (2005) Jasmonates and Na-orthovanadate promote resveratrol production in *Vitis vinifera* cv. Barbera cell cultures. New Phytologist 166:895-905. DOI 10.1111/j.1469-8137.2005.01383.x Watts K T, Lee P C, Schmidt-Dannert C (2006) Biosynthesis of plant-specific stilbene polyketides in metabolically engineered *Escherichia coli*. BMC Biotechnology 6:22. DOI 10.1186/1472-6750-6-22

Wenzel, E., and Somoza, V., (2005) Metabolism and bio-availability of trans-resveratrol. Mol. Nutr. Food Res. 49:472-481.

White, F. F et al., (1985) J. Bacteriol., vol. 164, p. 33.

Wink M, Alfermann A W, Franke R, Wetterauer B, Distl M, Windhovel J, Krohn O, Fuss E, Garden H, Mohagheghza-deh A, Wildi E, Ripplinger P (2005) Sustainable biopro-duction of phytochemicals by plant in vitro cultures: anticancer agents. Plant Gen Res. 3:90-100

Yan Q, Hu Z, Tan R X, Wu J (2005) Efficient production and recovery of diterpenoid tanshinones in *Salvia miltiorrhiza* hairy root cultures with in situ adsorption, elicitation and semi-continuous operation. J Biotechnol. 119:416-24

What is claimed is:

1. A method of increasing the production of a prenylated stilbenoid from hairy root culture material through biosynthesis, the method comprising:
   contacting the hairy root culture material capable of producing the prenylated stilbenoid with a precursor of the prenylated stilbenoid;
   thereby producing an increased amount of the prenylated stilbenoid compared to the method in which the precursor is not contacted with the hairy root culture material; and
   wherein the precursor comprises piceatannol and further comprising contacting the hairy root culture material with methyl jasmonate and piceatannol.

2. A method of increasing the production of a prenylated stilbenoid from hairy root culture material through biosynthesis, the method comprising:
   contacting the hairy root culture material capable of producing the prenylated stilbenoid with a cyclodextrin and methyl jasmonate;
   thereby producing an increased amount of the prenylated stilbenoid compared to the method in which the cyclodextrin and methyl jasmonate are not contacted with the hairy root culture material;
   wherein the hairy root culture material is contacted with the methyl jasmonate and a precursor comprising piceatannol.

3. The method of claim 2, the hairy root culture material further comprising grape hairy roots.

4. The method of claim 2, the hairy root culture material further comprising peanut hairy roots.

5. The method of claim 2 wherein said prenylated stilbenoid product of interest comprises arachidin.

6. The method of claim 2 wherein methyl jasmonate and the cyclodextrin contact the hairy root culture material for at least one hour.

7. The method of claim 1 wherein said prenylated stilbenoid product of interest comprises arachidin.

8. The method of claim 1 wherein the methyl jasmonate, piceatannol and a cyclodextrin contact the hairy root culture material for at least one hour.

9. A method of increasing the production of a prenylated stilbenoid from hairy root culture material through biosynthesis, the method comprising:
   contacting the hairy root culture material capable of producing the prenylated stilbenoid with a precursor of said prenylated stilbenoid product of interest, a cyclodextrin, and a methyl jasmonate;
   thereby producing an increased amount of the prenylated stilbenoid compared to the method in which the precursor is not contacted with the hairy root culture material;
   wherein the precursor comprises piceatannol.

10. The method of claim 9 wherein said prenylated stilbenoid product of interest comprises arachidin.

11. The method of claim 9 wherein the methyl jasmonate, piceatannol and the cyclodextrin contact the hairy root culture material for at least one hour.

* * * * *